(12) United States Patent
Komatsu et al.

(10) Patent No.: US 6,515,296 B1
(45) Date of Patent: Feb. 4, 2003

(54) PATTERN DIMENSION MEASURING SYSTEM AND PATTERN DIMENSION MEASURING METHOD

(75) Inventors: Fumio Komatsu, deceased, late of Fuchu (JP), by Tomoko Komatsu, sole heir; Motosuke Miyoshi, Tokyo-To (JP); Katsuya Okumura, Yokohama (JP)

(73) Assignee: Kabushiki Kaisha Toshiba, Kawasaki (JP)

(*) Notice: Subject to any disclaimer, the term of this patent is extended or adjusted under 35 U.S.C. 154(b) by 0 days.

(21) Appl. No.: 09/570,538

(22) Filed: May 12, 2000

(30) Foreign Application Priority Data

May 14, 1999 (JP) .......................................... 11-134971

(51) Int. Cl.[7] .............................................. G01N 23/00
(52) U.S. Cl. .................................. 250/559.44; 250/311
(58) Field of Search ................................ 250/548, 558, 250/559.01, 594.44, 559.3, 201.2, 550, 574, 201.3, 201.4, 201.8, 202, 491.1, 310, 311

(56) References Cited

U.S. PATENT DOCUMENTS 5,430,292 A * 7/1995 Honjo et al. ................. 250/310
6,172,363 B1 * 1/2001 Shinada et al. ............. 250/310
6,184,526 B1 * 2/2001 Kohama et al. ............ 250/310

OTHER PUBLICATIONS

E. Munro, Optik, vol. 39, No. 4, pp. 450–466, "Calcuation of the Optical Properties of Combined Magnetic Lenses and Deflection Systems with Superimposed Fields," 1974.

* cited by examiner

Primary Examiner—Robert H. Kim
Assistant Examiner—Hoon K. Song
(74) Attorney, Agent, or Firm—Oblon, Spivak, McClelland, Maier & Neustadt, P.C.

(57) ABSTRACT

In an operation of a pattern dimension measuring system comprising a stage, an electron gun part, electron lens systems for scanning electron beam on a sample and having a MOL mechanism thereto, a secondary electron detector for detecting secondary electrons and so forth emitted from the sample, and a host computer having a pattern dimension measuring part, the stage is moved at a constant velocity, the coordinates of the stage is measured by a laser interferometer in real time, the variation in working distance of the electron beam is measured in real time by the optical lever system from a focal length measuring part to be fed back to a stage control part and an objective lens. When a pattern serving as an object to be measured reaches a region capable of scanning, the electron beam is scanned in the best focus while moving the scanning start position of the electron beam in synchronism with the constant velocity movement of the stage, so that the SEM image thereof is acquired.

14 Claims, 17 Drawing Sheets

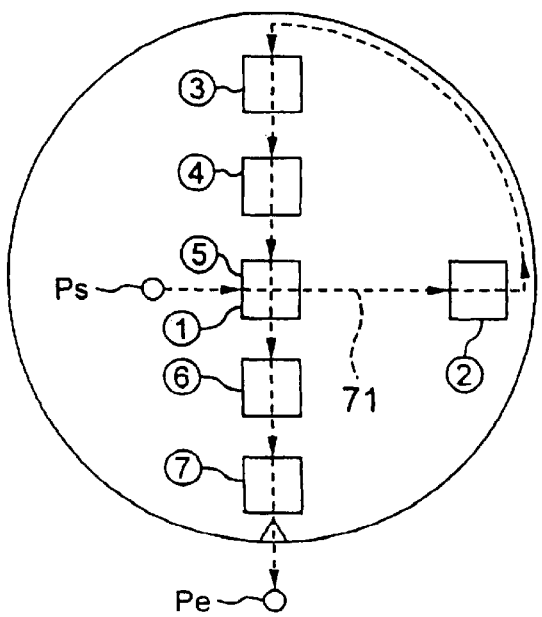
FIG. 2 *PRIOR ART*
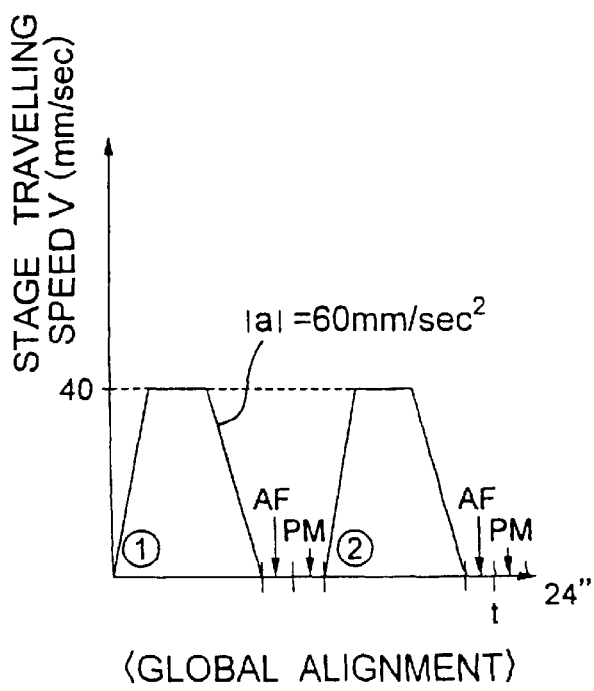
FIG. 3A
*PRIOR ART*
⟨GLOBAL ALIGNMENT⟩
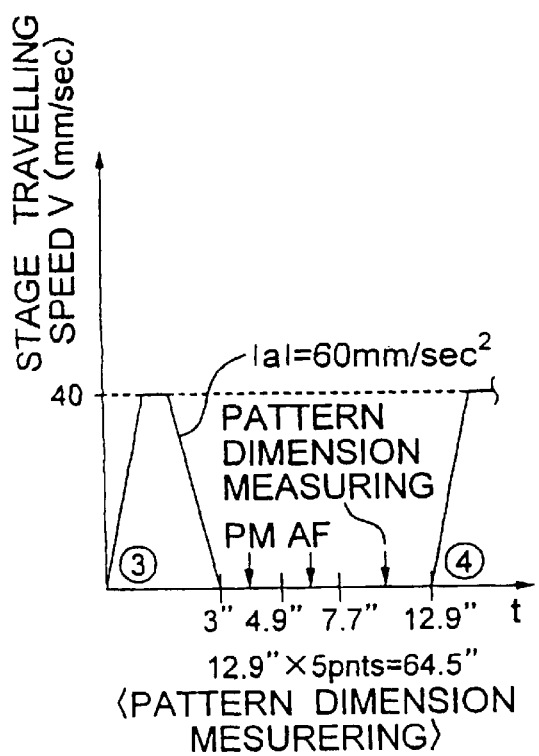
FIG. 3B
*PRIOR ART*
⟨PATTERN DIMENSION MESURERING⟩

(GLOBAL ALIGNMENT)

(PATTERN DIMENSION MESURING)

| LENGTH MEASUREMENT CONDITIONS | LENGTH MEASURED NUMBER (A) BY CONVENTIONAL LENGTH MEASURING SEQUENCE | LENGTH MEASURED NUMBER (B) BY LENGTH MEASURING SEQUENCE IN CONSTANT VELOCITY STAGE MOVEMENT | RATE OF IMPROVEMENT B/A |
|---|---|---|---|
| IN-PLANE 9-POINT LENGTH MEASUREMENT (3pnts/3shots) | 21W/Hr | 42W/Hr | 2.0 TIMES |
| IN-PLANE 15-POINT LENGTH MEASUREMENT (5pnts/3shots) | 14W/Hr | 42W/Hr | 3.0 TIMES |
| IN-PLANE 25-POINT LENGTH MEASUREMENT (5pnts/5shots) | 9W/Hr | 31W/Hr | 3.4 TIMES |
| IN-PLANE 45-POINT LENGTH MEASUREMENT (9pnts/5shots) | 5W/Hr | 31W/Hr | 6.2 TIMES |

FIG. 19

PATTERN DIMENSION MEASURING SYSTEM AND PATTERN DIMENSION MEASURING METHOD

BACKGROUND OF THE INVENTION

1. Field of the Invention

The present invention relates generally to a pattern dimension measuring system and a pattern dimension measuring method. More specifically, the invention relates to a system and method for measuring the dimensions of a pattern formed on the surface of a sample, while moving a stage, on which the sample is mounted.

2. Description of the Prior Art

In recent years, pattern dimension measuring systems are widely utilized for measuring the dimensions of a pattern formed on the surface of a semiconductor device, such as a very large scale integration (VLSI).

Referring to the accompanying drawings, a conventional pattern dimension measuring system will be described below. Furthermore, in the following drawings, the same reference numbers are assigned to the same portions, and the descriptions thereof are suitably omitted.

FIG. 1 is a schematic block diagram showing an example of a conventional pattern dimension measuring system. In this figure, a pattern dimension measuring system 110 comprises an electron beam lens-column 111, a vacuum sample chamber 2 and a host computer 104.

The electron beam lens-column 111 includes an electron gun part 11 and an electron lens system, and has a resolving power of about 5 nm corresponding to the scale down of semiconductor devices. The electron gun part 11 is designed to irradiate a sample 5 with electron beam 96. The electron lens system has a condenser lens 21, a deflecting lens 102 and an objective lens 103. The electron lens system is designed to control the trajectory and focal length of the electron beam 96 so that the electron beam 96 focuses on the sample 5.

The vacuum sample chamber 2 houses an X-Y stage 3, a sample conveyance system 12 and a secondary electron detector 31 in vacuum atmosphere. The sample conveyance system 12 is designed to convey a sample 5, such as a semiconductor wafer, to the X-Y stage 3. The X-Y stage 3 is designed to support the conveyed wafer 5 (sample) on the upper surface thereof, and to move in an optional direction on the X-Y plane with a high stopping accuracy of about 1 $\mu$m on the basis of a control signal supplied from a stage control part 113. The secondary electron detector 31 is designed to detect secondary electrons, reflected electrons and back scattered electrons (which will be hereinafter referred to as "secondary electrons and so forth"), which are emitted from the surface of the sample 5 irradiated with the electron beam 96, to supply the detected results to an image data processing part 132. The image data processing part 132 is designed to receive the detected results of the secondary electron detector 31 to supply image data, which form a SEM image by a predetermined data processing, to the host computer 104. The host computer 104 has a pattern dimension calculating part 16 for calculating the dimensions of a target pattern on the basis of the image data, which are fed from the image data processing part 132, to suitably store the calculated results in a memory 14.

Referring to FIG. 2, an example of a sequence for measuring the dimensions of a pattern, which is formed on the surface of the wafer 5 using the pattern dimension measuring system 110 shown in FIG. 1, will be described below. FIG. 2 is a schematic diagram showing the moving direction of the X-Y stage 3. In this example, the stage 3 is designed to move from a measurement start position Ps to a measurement end position Pe while drawing a locus shown by the dotted line in FIG. 2.

First, by the sample conveyance system 12, the wafer 5 is conveyed into the vacuum sample chamber 2 to be mounted on the upper surface of the X-Y stage 3.

Then, global alignment marks ① and ②, which are formed on the surface of the wafer 5 at substantially center and peripheral portion thereof, respectively, are used to carry out the global alignment to calculate a correlation between a pattern layout coordinate system and a stage coordinate system on the wafer 5.

Then, the stage 3 is moved so that the position of a target pattern to be measured, e.g., the vicinity of pattern ③ shown in FIG. 2, is a position irradiated with the electron beam 96, and stopped at this position. Then, the exciting current of the objective lens 103 is controlled so that the edges of the target pattern are within a beam focal depth by the automatic focus. Then, while the stage 3 is moved again in the direction of the dotted line arrow in FIG. 2, the electron beam 96 is scanned on the pattern ③ to detect secondary electrons and so forth, which are emitted from the surface of the wafer 5, by unit of the secondary electron detector 31. The detected signal is data-processed by the image data processing part 132 to be inputted to the host computer 104 as an image signal constituting a SEM image. The host computer 104 detects the target pattern ③ existing in the SEM image by the pattern recognition processing. The pattern dimension calculating part 16 in the host computer 104 detects the bottom edges of the detected target pattern ③ on the basis of the optimum measuring algorithm to measure the dimensions of the pattern. Moreover, if the next target pattern (④-⑦) exists, the X-Y stage 3 is moved again toward the next target pattern to be stopped again in the vicinity thereof, and then, the above described operations are repeated. Such a series of operations are controlled by the host computer 104 in accordance with a sequence which is set by a recipe file stored in the memory 14 of the pattern dimension measuring system or the like.

However, in the above described sequence, the measurement of the dimensions is carried out by repeating the movement and stopping of the X-Y stage 3 any number of times, so that it takes a lot of processing time in the case of a multipoint measurement for measuring the dimensions of patterns at a large number of measuring places.

FIGS. 3A and 3B are graphs for explaining the throughput, of the pattern dimension measuring system shown in FIG. 1, and show the variation in stage traveling speed. It can be also understood from FIGS. 3A and 3B that the stage 3 is stopped in front of the global alignment mark and the pattern to be measured for focusing (AF) and pattern recognition (PM).

Particularly in recent years, the need for multipoint measurement is enhanced (a) at the initial stage of the development of process devices, (b) in the evaluation of the lens aberration of an aligner and in the evaluation of a wafer for making exposure conditions, and (c) due to the increase of the number of measured points as the increase of the diameter of the wafer. However hand, the throughput in the above described sequence is 30 wafers/hour to 40 wafers/hour, so that there is a problem in that it takes several hours to carry out a multipoint measurement even with a full automatic measurement in the present circumstances.

SUMMARY OF THE INVENTION

It is a first object of the present invention to provide a pattern dimension measuring system with a high throughput.

It is a second object of the present invention to provide a pattern dimension measuring method with a high throughput.

According to the first aspect of the present invention, there is provided; a pattern dimension measuring system comprising: a movable stage for mounting a sample on the upper surface thereof, the sample having a pattern to be measured formed thereon; a first control unit for moving the stage; an electron beam irradiation unit for irradiating the sample with an electron beam; an electron beam deflecting/scanning unit for deflecting and scanning the electron beam in a region on the sample, the region including a first portion normally scanned with the electron beam along and around an outgoing beam axis, and a second portion outside the first portion, the second portion being scanned with the electron beam deflected apart from and in parallel to the outgoing beam axis and; a stage coordinate detecting unit for detecting X-Y coordinates of the stage; a secondary electron detecting unit for detecting a secondary electron and a deflected electron which are emitted from the sample by an irradiation with the electron beam and for outputting an image signal which forms an electron image, the electron image representing a shape of the surface of the sample; a pattern dimension calculating unit for obtaining a dimension of the pattern to be measured by recognizing side edges thereof using the image signal and by calculating the dimension thereof; and a second control unit for controlling the first control unit so that the stage continuously moves without stopping and for controlling the electron beam deflecting/scanning unit using the detected result of the stage coordinate detecting unit so that the electron beam is scanned while a scanning start position thereof moves in synchronism with movement of the stage.

According to the present invention, due to a continuous movement of the stage in measurement, it is possible to measure the dimensions of a pattern on a sample with a high throughput.

In a preferred embodiment of the pattern dimension measuring system according to the invention, the pattern dimension measuring system further comprises a focal length measuring unit for detecting a focal length of the electron beam deflecting/scanning unit, and, the second control unit receives the detected result of the focal length measuring unit and optimizes the focal length of the electron beam deflecting/scanning unit on the basis thereof while the stage moves continuously at a constant velocity.

It is preferable that the electron beam deflecting/scanning unit scans each frame to which the pattern to be measured is divided, the frame being defined by the maximum deflection width thereof, and that any one of a continuous scanning mode, in which the plurality of frames are continuously scanned, and a frame accumulating mode, in which the same frame is scanned a plurality of time to output the optimum pattern dimensions, is able to be selected.

The region on the sample preferably further includes a third portion where the image signal is to be acquired and a fourth portion where an irradiation with the electron beam is to be stopped, and the second control unit preferably supplies a control signal to the first control unit so that the stage moves at a first velocity in a third portion of the region and moves at a second velocity which is higher than the first velocity in a fourth portion of the region.

Furthermore, the second control unit sets the second velocity on the basis of a correlation between a distance between the patterns to be measured and on the basis of a processing time required for recognizing a pattern by the pattern dimension calculating unit.

In another preferred embodiment of the invention, the pattern dimension measuring system further comprises image processing unit for processing the image signal so that the electron image is a mirror image with respect to the central axis-in X or Y directions in accordance with a variation in-moving direction of the stage.

According to the second aspect of the invention, there is provided; a pattern dimension measuring method using a pattern dimension measuring system comprising: a movable stage for mounting thereon a sample, on which a pattern to be measured is formed; a stage coordinate detecting unit for detecting X-Y coordinates of the stage; a electron beam irradiation unit for irradiating the sample with an electron beam; an electron beam deflecting/scanning unit for deflecting and scanning the electron beam on the sample; a focal length measuring unit for detecting a focal length of the electron beam deflecting/scanning unit; a secondary electron detecting unit for detecting a secondary electron and a deflected electron which are emitted from the sample by the irradiation with the electron beam and for outputting an image signal which forms an electron image; and a pattern dimension calculating unit for calculating a dimension of the pattern by recognizing side edges of the pattern using the image signal and by calculating the dimension of the pattern, the pattern dimension measuring method comprising: a first step of calculating a correlation between a coordinate system of the stage and a pattern layout coordinate system; a second step of detecting the position of a pattern to be measured on the basis of the correlation while the stage moves-continuously without stopping; a third step of detecting the variation in distance between the sample and the electron beam irradiation unit due to movement of the stage, and optimizing the focal length of the electron beam deflecting/scanning unit before the pattern to be measured reaches an area in which the electron beam can be scanned; a fourth step of acquiring an electron image of the pattern to be measured, by deflecting the electron beam in synchronism with the movement of the stage, and by scanning the electron beam in a region including a region, the region including a first portion normally scanned with the electron beam along and around an outgoing beam axis, and a second portion outside the first portion, the second portion being scanned with the electron beam deflected apart from and in parallel to the outgoing beam axis; and a fifth step of recognizing the pattern to be measured, using the electron image, and calculating the dimensions thereof by a predetermined algorithm.

According to a pattern dimension measuring method of the present invention, the detection of the position of a pattern to be measured and the adaptation of the focus of electron beam is processed in real time even during the movement of a stage, so that it is not required to stop the stage before incorporating a SEM image. Therefore, it is possible to measure the dimensions of a pattern while moving the stage at a constant velocity.

In addition, since the scanning range of the electron beam can be enlarged to a range where all of beam trajectories are away from the outgoing beam axis, it is possible to scan electron beam on a pattern to be measured, in synchronism with the constant velocity movement of the stage. Thus, it is possible to further increase the traveling speed of the stage, so that it is possible to improve the throughput in the pattern dimension measurement. On the other hand, when the traveling speed of the stage remains being relatively low, it is possible to scan electron beam on the same pattern to be measured, several times. Thus, it is possible to further enhance the accuracy of the dimension measurement.

In a preferred embodiment of the invention, the pattern includes a reference pattern serving as a reference of the detection of the pattern to be measured, the correlation includes a relationship between a position of the reference pattern and a positions of the pattern to be measured, and the second step includes a step of detecting the position of the reference pattern on the basis of the correlation, and detecting the position of the pattern to be measured on the basis of the detected position of the reference pattern and the relationship between the detected position of the reference pattern and the position of the pattern to be measured.

Furthermore, the fourth step may include a step of dividing the pattern to be measured to a plurality of frames, the frame being defined by the maximum deflection width of the electron beam deflecting/scanning unit, and continuously scanning the plurality of frames (a continuous scanning step) or alternatively, scanning the same frame a plurality of times and outputting an optimum pattern dimension (a frame integrating step).

Thus, when a continuous scanning procedure is selected, it is possible to improve the throughput in the pattern dimension measurement. On the other hand, when a frame accumulating procedure is selected, it is possible to improve S/N.

In the above mentioned pattern dimension measuring method, the region on the sample may include a third portion where the image signal is to be acquired and a fourth portion where no electron beam is to be irradiated, and the stage may be moved at a first constant velocity in the third region on the sample and at a second constant velocity which is higher than the first constant velocity in the fourth portion of the region after an irradiation of the electron beam is stopped and before an irradiation with the electron beam is restarted.

Thus, it is possible to enhance the throughput in the dimension measurement.

The second velocity may be set on the basis of a correlation between a distance between the patterns to be measured and on the basis of a processing time required for recognizing a pattern by the pattern dimension calculating unit.

Thus, in accordance with the specification of a measuring system, to which a pattern dimension measuring method according to the present invention is applied, it is possible to complete a dimension measurement processing until the acquisition of the electron image of the next pattern to be measured is started after the acquisition of the electron image of a certain pattern to be measured.

The fourth step may include a step of processing the image signal so that the electron image is a mirror image with respect to the central axis in X or Y directions in accordance with a variation in moving direction of the stage.

Thus, it is possible to reduce the time required to carry out the above described pattern recognition and dimension calculating processing, and it is possible to further improve the throughput in the dimension measurement.

The second step may be a step of detecting a position of the pattern to be measured, at a first measuring magnification, and the fourth step may be a step of acquiring the electron image at a second measuring magnification which is greater than the first measuring magnification.

BRIEF DESCRIPTION OF THE DRAWINGS

In the drawings:

FIG. 2 is a schematic diagram for explaining a conventional pattern dimension measuring method;

FIGS. 3A and 3B are graphs for explaining the throughput of the pattern dimension measuring system shown in FIG. 1;

FIG. 19 is a table showing throughput in a pattern dimension measuring method according to the present invention, in comparison with the prior art.

DESCRIPTION OF THE PREFERRED EMBODIMENTS

Referring now to the accompanying drawings, some preferred embodiments of the present invention will be described below.

(1) Preferred Embodiment of Pattern Dimension Measuring System

Figure 4:
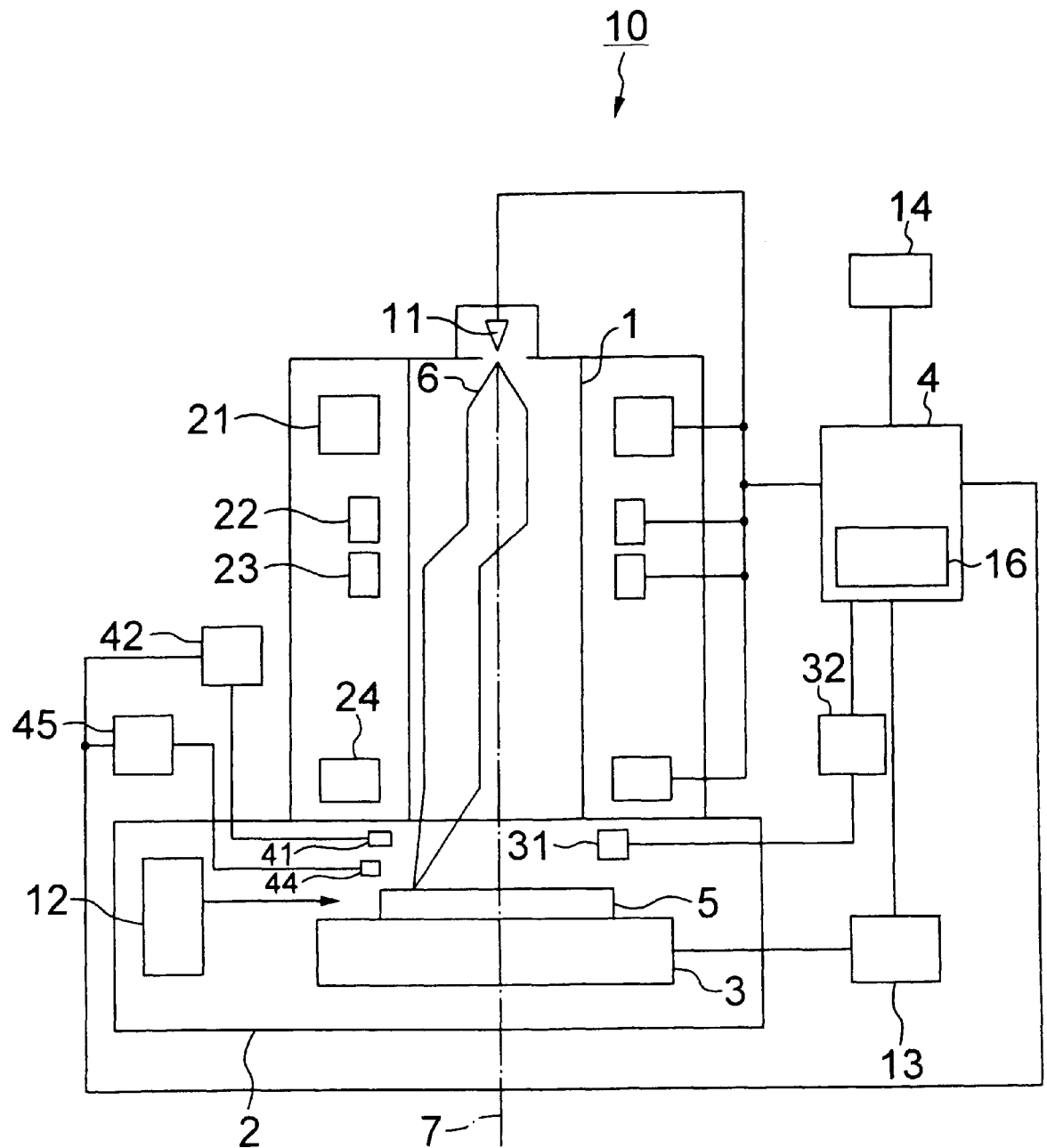
FIG. 4 is a schematic block diagram of a preferred embodiment of a pattern dimension measuring system according to the present invention.

FIG. 4 is a block diagram schematically showing a preferred embodiment of a pattern dimension measuring system according to the present invention. This preferred embodiment is characterized in that a scanning electron microscope (SEM) image of a target pattern is acquired to measure the dimensions of the pattern while moving a stage at a constant velocity.

Figure 1:
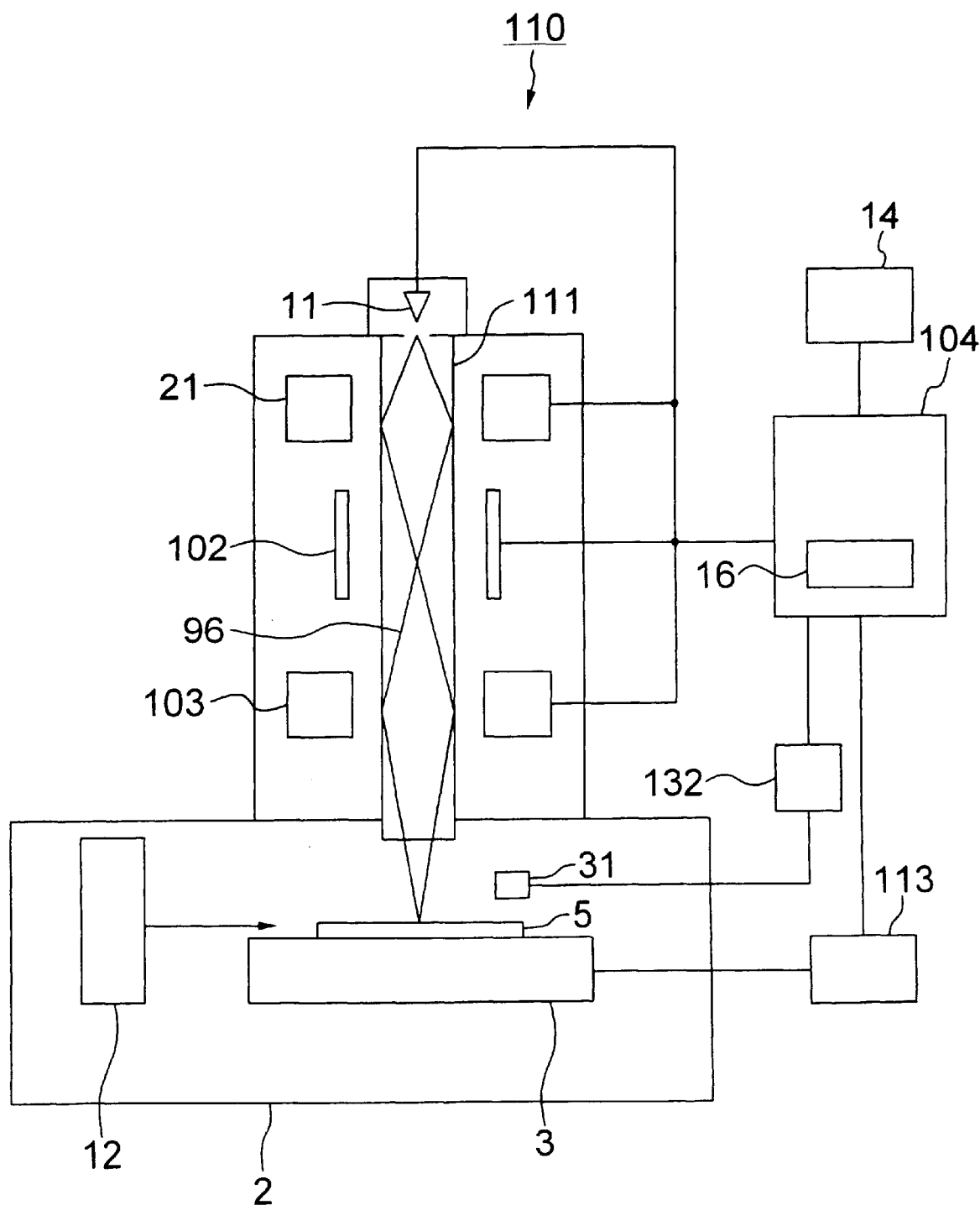
FIG. 1 is a schematic block diagram showing an example of a conventional pattern dimension measuring system.

As can be understood from the comparison with FIG. 1, a pattern dimension measuring system 10 shown in FIG. 4 comprises two deflecting lenses 22 and 23, an objective lens 24, a laser interferometer 41, a laser interferometer control part 42, a stage control part 13, a focal length measuring part 44, a control part 45 for controlling the part 44, an image data processing part 32, and a memory 14. The memory 14 has stored therein a recipe file which will be described later. Other constructions of the pattern dimension measuring system 10 shown in FIG. 4 are substantially the same as those of the pattern dimension measuring system shown in FIG. 1.

The laser interferometer 41 is designed to detect the coordinates of a stage 3 in accordance with a control signal, which is supplied from the laser interferometer control part 42, to supply the detected results to a host computer 4 in real time even during the movement of the stage 3. On the basis of the detected results, the host computer 4 is designed to calculate correction parameters, which are used for correcting pitching, yawing and so forth, which may occur in accordance with the movement of the stage. The host computer 4 is also designed to supply control signals including the correction parameters to the stage control part 13 in real time. The stage control part 13 is designed to move the stage 3 at a constant velocity in accordance with the control signals.

In this preferred embodiment, the pattern dimension measuring system 10 is designed to move the stage 3 at a constant velocity of, e.g., 10 mm/sec. The moving amount of the stage 3 at this velocity corresponds to 80 $\mu$m/frame which is the moving amount of a stage when electron beam 6 is scanned at a scanning speed four times as high as the scanning speed of TV in order to acquire an image of one frame (512×512 pixels, 512 scans).

The scanning speed of the electron beam 6 is conventionally executed by the TV scan (16 kHz/scan). In this preferred embodiment, the pattern dimension measuring system 10 scans the electron beam 6 at a high speed of 64 kHz/scan in order to realize a beam scanning in synchronism with the traveling speed of a constant velocity stage, so as to correspond to the movement of the stage 3. This scanning speed corresponds to a speed of 8 msec/frame with respect to the scanning of one frame (512 scans).

The objective lens 24 has the function of MOL (Moving Objective Lens; E. Munro, "Calculation of the Optical Properties of Combined Magnetic Lens and Deflection Systems with Superimposed Fields", OPTIK, pp.450–466, 39 (1974)) in order to realize the beam scanning in synchronism with the movement of the stage at a constant velocity. The MOL mechanism is a mechanism for irradiating the surface of the sample 5 with the electron beam 6 so that the electron beam 6, which is incident from the outside of the axis, i.e., apart from the central axis, of the objective lens 24 while being greatly deflected by a deflecting system, are in parallel to the outgoing beam axis by the superimposed magnetic field caused by a superimposing lens in the objective lens 24. According to the present invention, the MOL mechanism is used to shift the electron beam 6 while synchronizing the electron beam 6 with the stage traveling speed.

Figure 5:
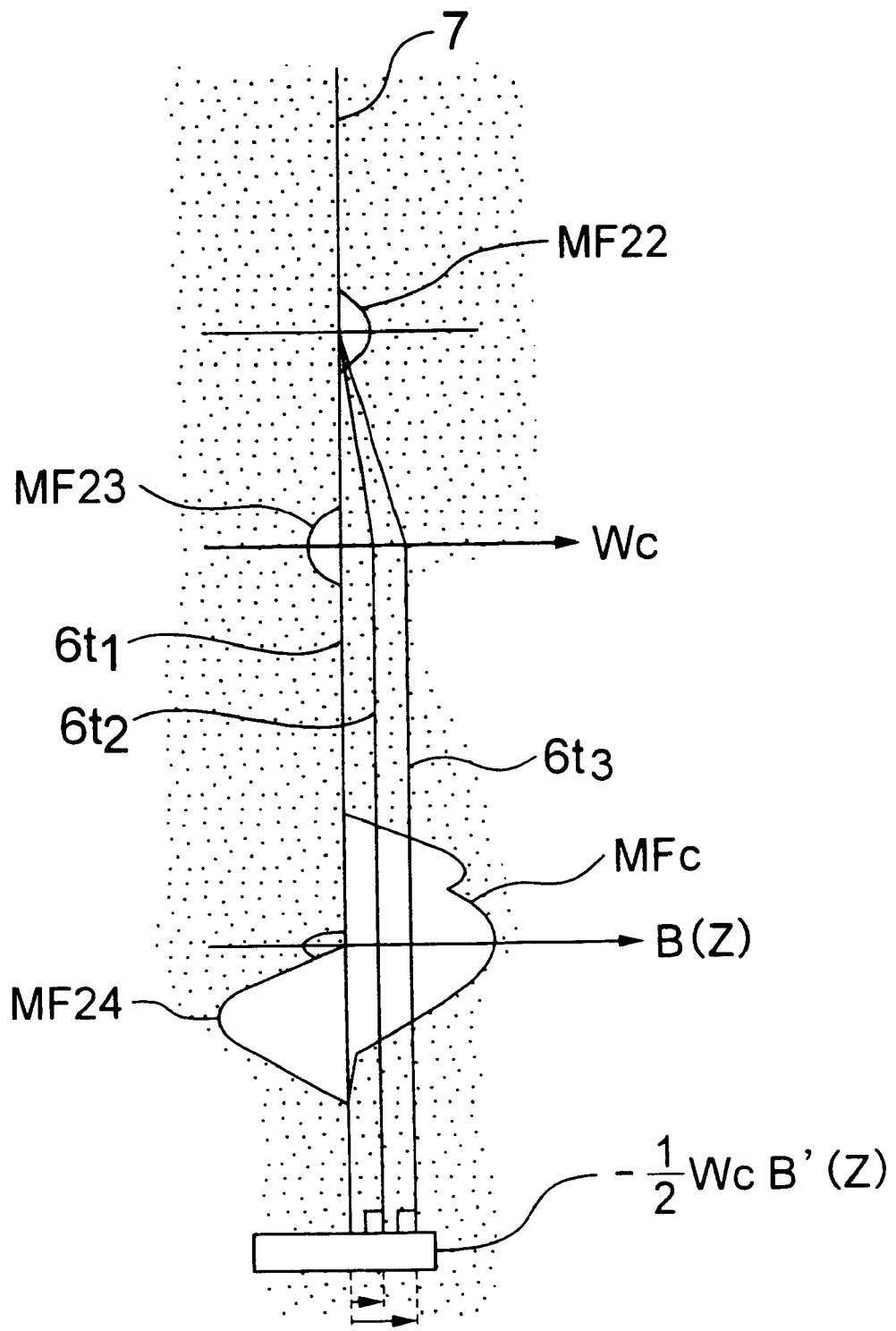
FIG. 5 is a conceptual diagram for explaining a MOL mechanism of the pattern dimension measuring system shown in FIG. 1.

FIG. 5 is a conceptual diagram for explaining the MOL mechanism of the pattern dimension measuring system 10 in this preferred embodiment. This figure shows the trajectory of the electron beam 6 passing through the condenser lens 21 with the elapse of time ($t_1$–$t_3$). It can be seen from FIG. 5 that the electron beam 6 is perpendicularly incident on the sample 5 while remaining being in parallel to the outgoing beam axis by the objective lens 24, while being deflected by the first deflecting lens 22 and the second deflecting lens 23.

Assuming that the movable range of the beam irradiation position by the MOL mechanism in this preferred embodiment is ±350 $\mu$m, the details will be described. First, the electron beam 6 is deflected by the condenser lens 21 so as to be in parallel to the outgoing beam axis 7, and incident on the first deflecting lens 22. A predetermined exciting current is supplied to the first deflecting lens 22 by the control of the host computer 4 to form a magnetic field MF22. By this magnetic field MF22, the electron beam 6 is deflected so as to be directed to the outside of the outgoing beam axis 7. Then, the second deflecting lens 23 forms a magnetic field MF23, which is directed in the opposite direction to the magnetic field MF22, on the basis of the control of the host computer 4. Thus, the electron beam 6 deflected toward the outside of the axis once is deflected so as to have a trajectory which is spaced from the outgoing beam axis 7 and which is parallel to the outgoing beam axis 7 (see FIG. 4). By the control of the host computer 4, the objective lens 24 forms a superimposed magnetic field wherein the magnetic field MF serving as the objective lens 24 is superimposed on a correction magnetic field MFc. Thus, even if the electron beam 6 passing through the objective lens 24 deviates from the outgoing beam axis 7, the focus thereof is adapted, so that the electron beam 6 can be incident on the surface of the sample 5. Furthermore, in FIG. 5, Wc denotes the position of the electron beam 6 in deflected directions on the X-Y plane, and B(Z) denotes a magnetic field on Z-axis.

Referring to FIG. 1 again, the focal length measuring part 44 is designed to measure the working distance of the electron beam 6 at the irradiation position in real time by the optical ranging (optical lever) system on the basis of control signals fed from the focal length measurement control part 45, and to transmit the variation in working distance, which is produced with the movement of the stage 3, to the host computer 4 in real time. The host computer 4 is designed to feed back the variation in working distance to the exciting current of the objective lens 24 via the focal length measurement control part 45 in real time.

Since the variation in working distance is caused by the warp of the wafer 5, it is possible to reduce the variation in working distance to the minimum by, e.g., providing the stage 3 with an electrostatic chuck mechanism for holding the wafer 5. As a result, it is possible to reduce the control range of the exciting current of the objective lens 24 to the minimum, and it is also possible to prevent the influence of hysteresis.

The image data processing part 32 is capable of carrying out a so-called mirror inversion processing for converting and outputting so that a SEM image is a mirror image, which is symmetric with respect to the central axis thereof in X or Y directions, in accordance with the variation in moving direction of the stage 3. Thus, when the moving direction of the stage 3 is reversed, it is possible to continue to carry out the multipoint measurement without taking account of the influence of the variation in direction.

The memory 14 stores therein a recipe file, in which measuring conditions, measuring sequence, which will be described later, and so forth are incorporated as a program.

The measuring conditions include, in addition to the above described traveling speed of the stage 3 and the above described scanning speed of the electron beam 6, the position of global alignment, which will be described later, the aligned position of a chip, the region of the pattern formed on each of chips, the region for forming a chip serving as an object to be measured and a pattern, the line width and pore size for pattern recognition, a measuring algorithm for detecting the bottom edges of the pattern to be measured, and so forth.

Referring to the accompanying drawings, as the first and second preferred embodiments of a pattern dimension measuring method according to the present invention, the operation of the pattern dimension measuring system 10 shown in FIG. 4 will be described below.

(2) First Preferred Embodiment of Pattern Dimension Measuring Method

First, the first preferred embodiment of a pattern dimension measuring method according to the present invention will be described below. This preferred embodiment is characterized in that a reference pattern is first detected, and the same pattern to be measured is recognized on the basis thereof to measure the dimensions thereof.

Figure 6:
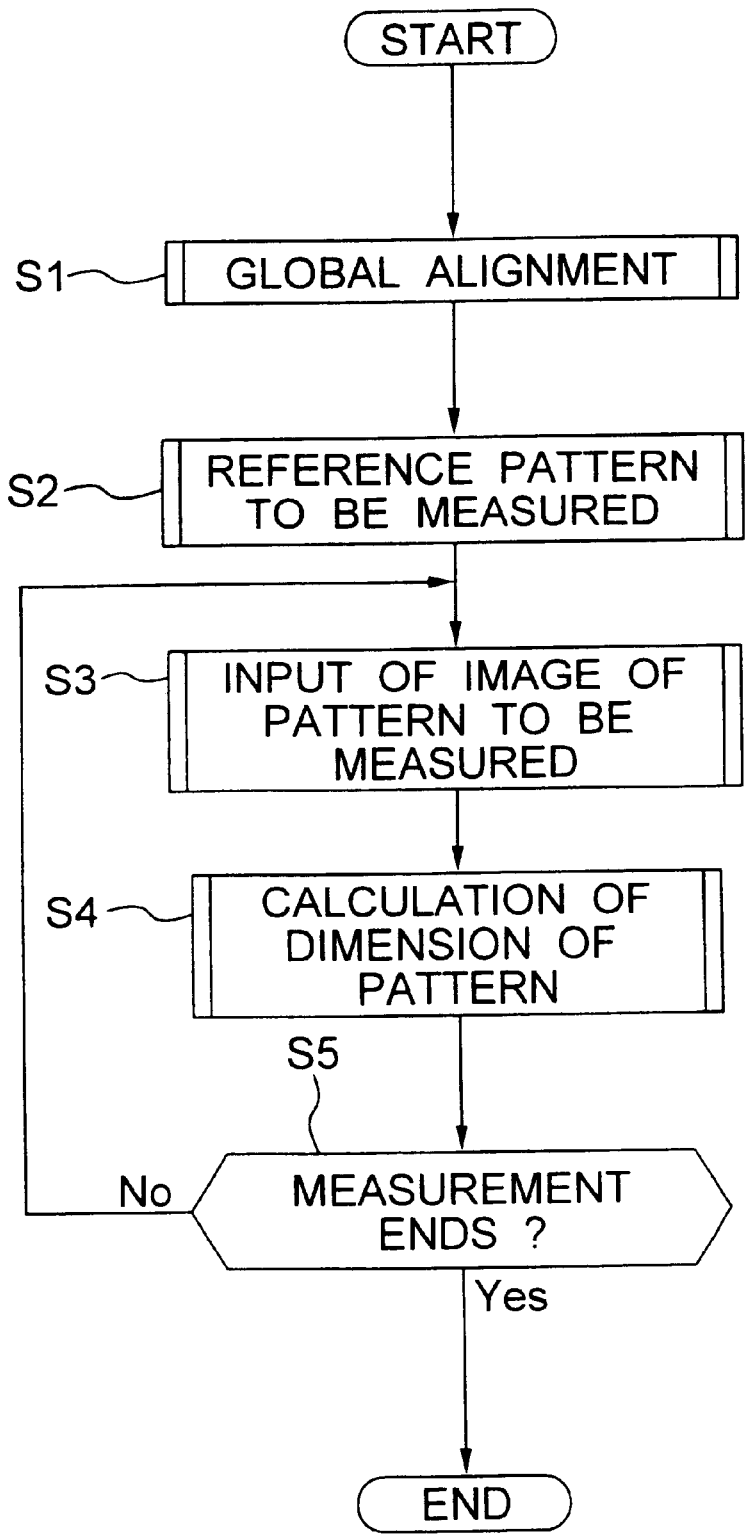
FIG. 6 is a flow chart for schematically explaining the first preferred embodiment of a pattern dimension measuring method according to the present invention.
Figure 7:
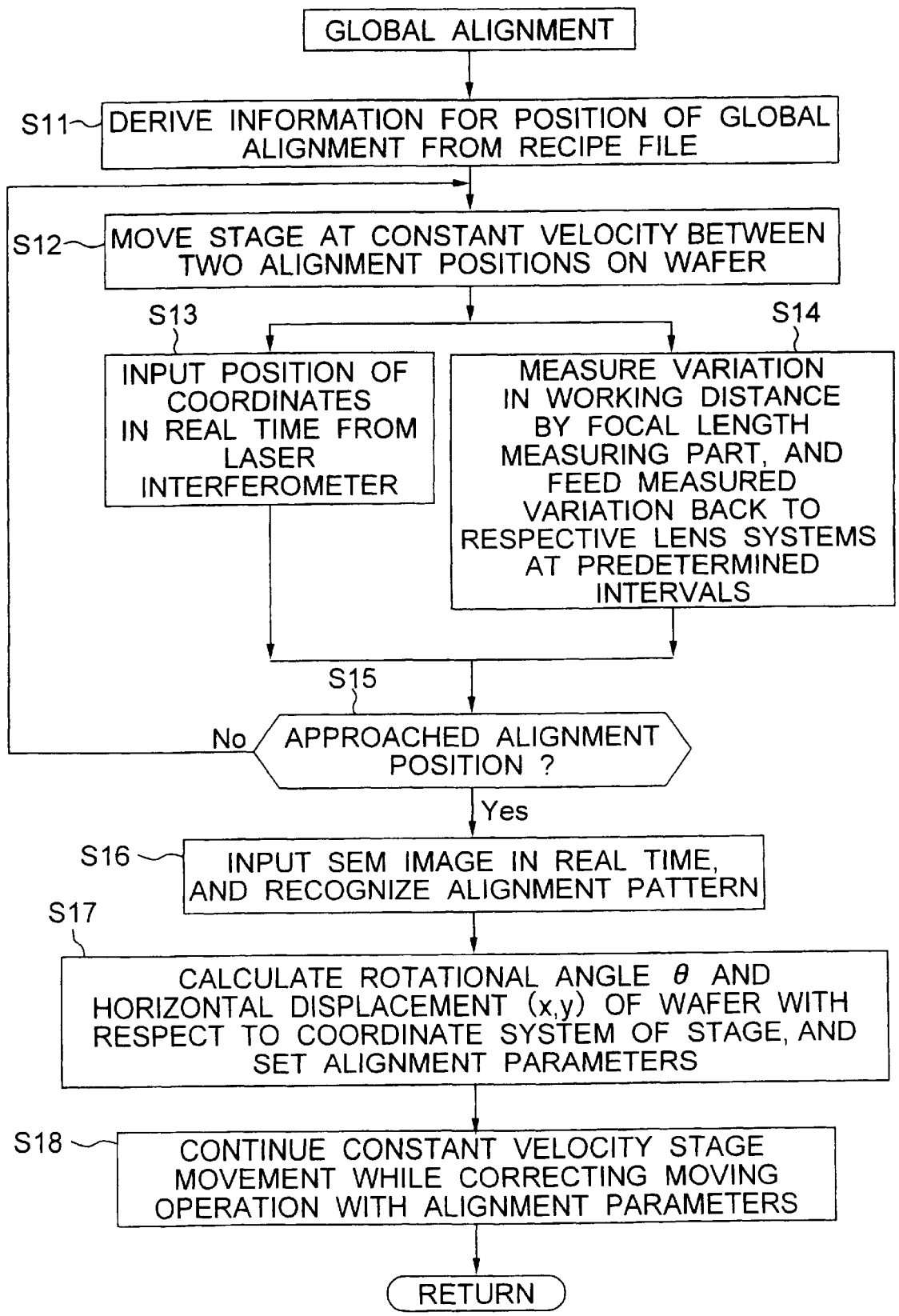
FIG. 7 is a flow chart for explaining the detailed procedure of a global alignment processing in the pattern dimension measuring method shown in FIG. 6.
Figure 8:
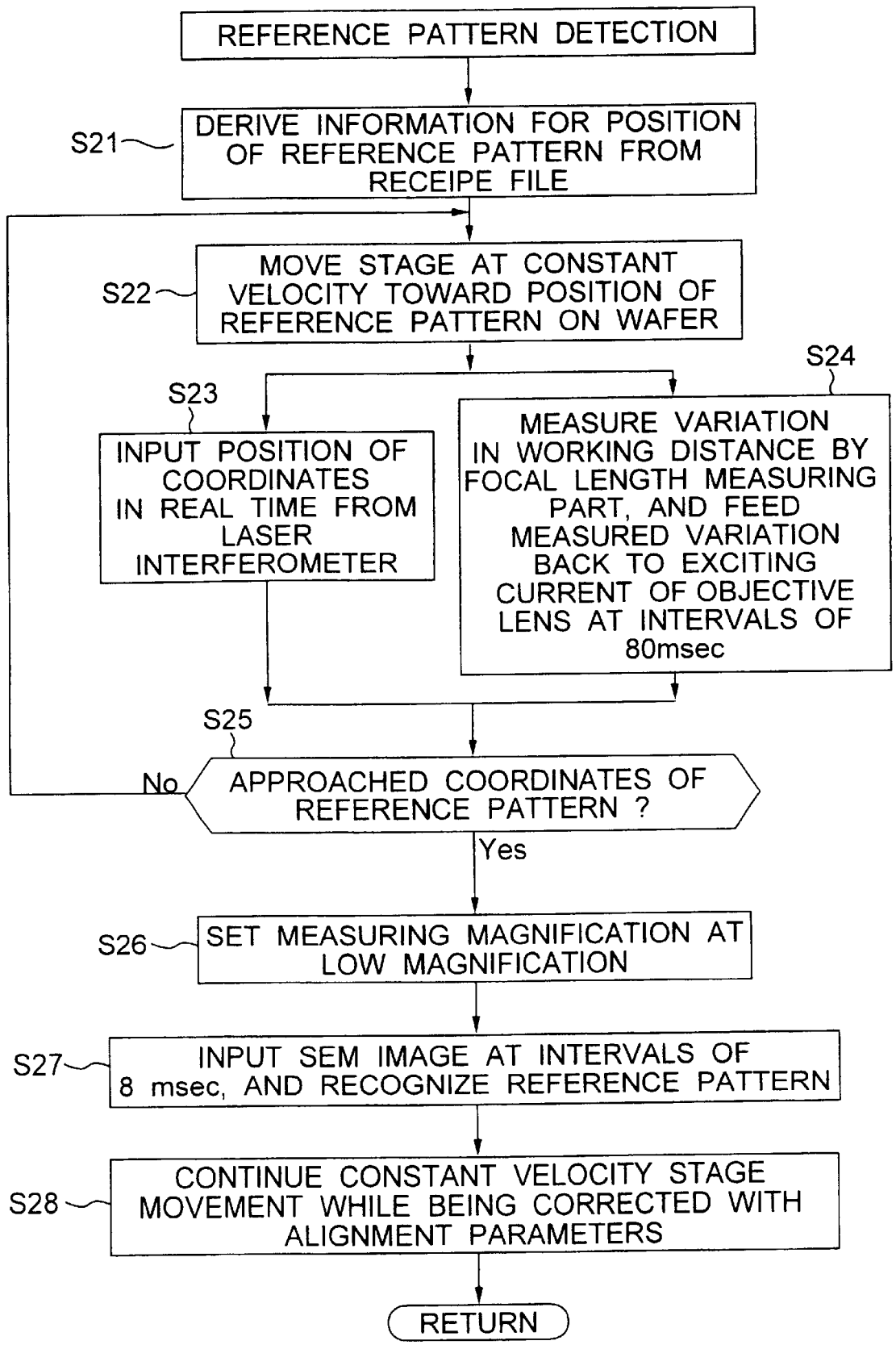
FIG. 8 is a flow chart for explaining the detailed procedure of a referent pattern detecting processing in the pattern dimension measuring method shown in FIG. 6.
Figure 9:
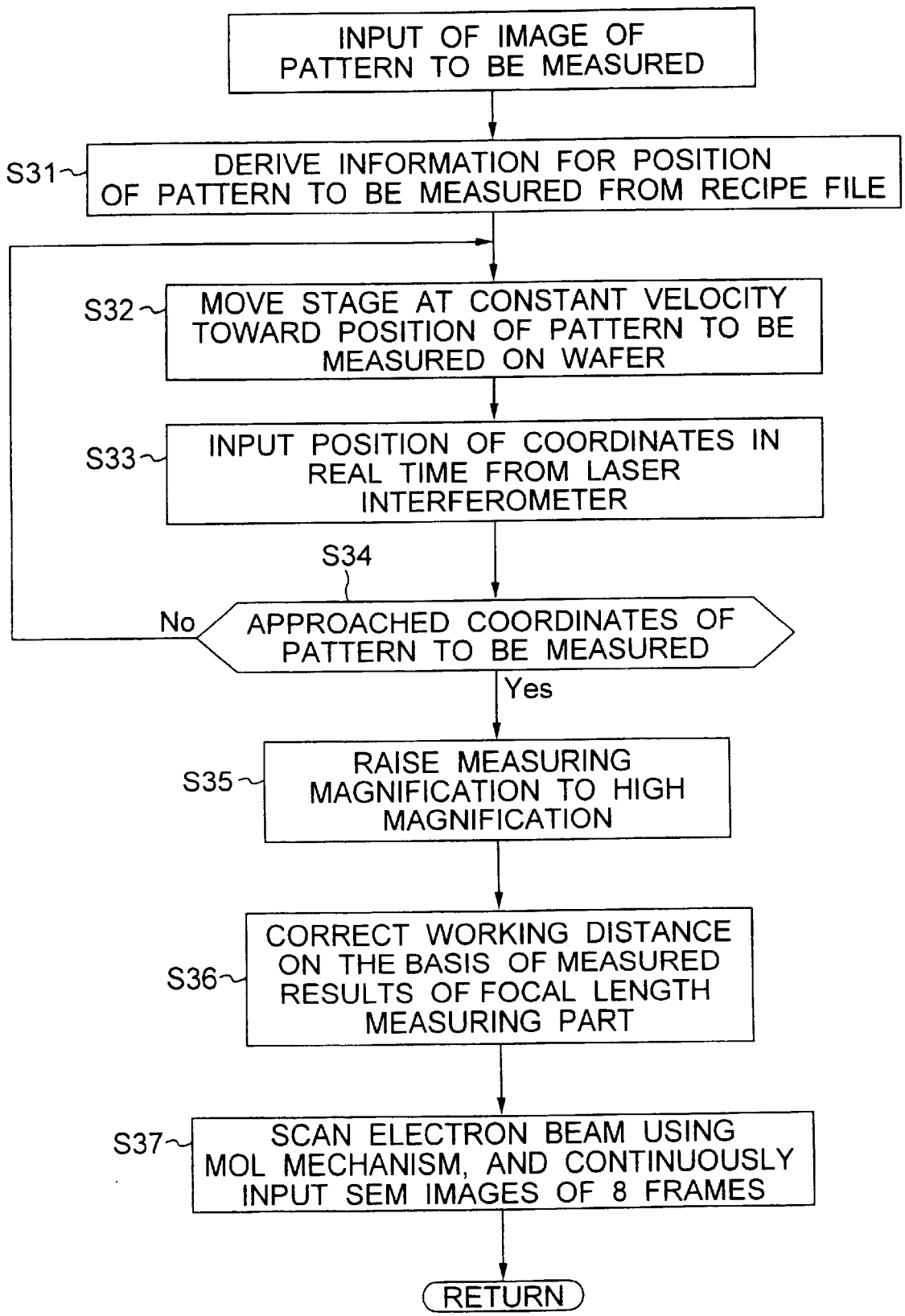
FIG. 9 is a flow chart for explaining the detailed procedure of a measuring pattern image inputting processing in the pattern dimension measuring method shown in FIG. 6.
Figure 10:
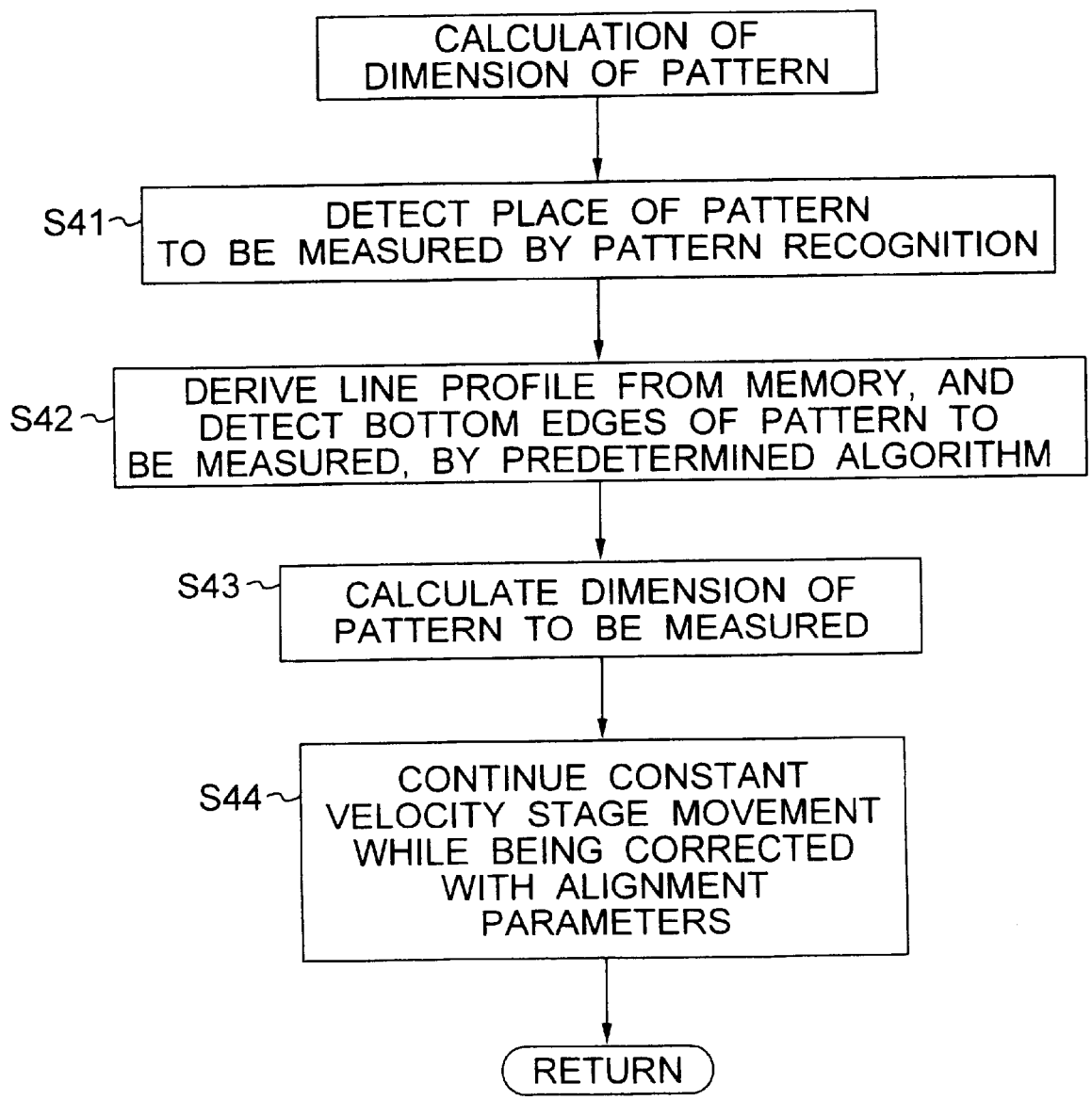
FIG. 10 is a flow chart for explaining the detailed procedure of a pattern dimension calculating processing in the pattern dimension measuring method shown in FIG. 6.

FIG. 6 is a flow chart for explaining the schematic procedure of a pattern dimension measuring method in this preferred embodiment, FIG. 7 is a flow chart for explaining the detailed procedure of a global alignment processing, FIG. 8 is a flow chart for explaining the detailed procedure of a reference pattern detecting processing, FIG. 9 is a flow chart for explaining the detailed procedure of a measuring pattern image inputting processing, and FIG. 10 is a flow chart for explaining the detailed procedure of a pattern dimension calculating processing.

As shown in FIG. 6, in this preferred embodiment, a correlation between a pattern layout coordinate system on the wafer 5 and a stage coordinate system is first acquired by a global alignment processing (step S1). Then, a position serving as a reference for recognizing a pattern to be measured is detected by a reference pattern detecting processing (step S2). Then, a region, in which the pattern to be measured is formed, is identified on the basis of the position, at which the reference pattern is detected, and the electron beam 6 is scanned in the identified region to carry out a measuring pattern image inputting processing (step S3). On the basis of the image, a pattern dimension calculating processing is carried out (step S4). The above described procedure at steps S3 and S4 is repeated times corresponding to the number of patterns to be measured (step S5).

Referring to the flow charts of FIGS. 7 through 10, the above described procedure at steps Si through S4 will be described in detail below.

1) Global Alignment Processing

After the wafer 5 is conveyed to the vacuum sample chamber 2 by unit of the wafer conveyance system 12, the global alignment processing is carried out on the basis of the SEM image. The position of the global alignment mark is previously set by a recipe file.

As shown in FIG. 7, information for the position of the global alignment mark is first derived from the recipe file stored in the memory 14 or the like (step S11). Then, the stage 3 is moved at a constant velocity between two alignment positions on the wafer 5 (step S12). In parallel to the movement of the stage 3, the information for the stage coordinates is inputted to the host computer 4 in real time by the laser interferometer 41 (step S13). In addition, the variation in working distance of the electron beam 6 is measured by the focal length measuring part 44 by the optical ranging system, and the measured results are fed back to the electron lens system via the host computer 4 at predetermined intervals (step S14). In this preferred embodiment, the feedback is carried out at intervals of time, in which the stage 3 travels over one chip, i.e., at intervals of 500 msec.

Then, after the stage 3 moves to the vicinity of the position of the alignment mark (step S15), the real time (intervals of 33 msec) input of the SEM image is started, and the pattern recognizing processing for the alignment pattern is carried out (step S16). In order to carry out the real time input, the image input synchronized with the above described constant velocity stage movement can be carried out if the SEM image is inputted at 350 µm/frame.

Then, the rotational angle (θ) and horizontal displacement (x, y) of the wafer 5 with respect to the stage coordinate system is calculated by the global alignment, and alignment parameters based thereon are set (step S17). Then, while the moving operation is corrected with the alignment parameters, the constant velocity stage movement is continued (step S18).

2) Reference Pattern Detection Processing

After the global alignment ends, the reference pattern detection processing is carried out.

As shown in FIG. 8, information for the reference pattern position is first derived from the recipe file (step S21). On the basis of this information, the stage 3 is moved at a constant velocity toward the position of the reference pattern on the wafer 5 (step S22). Even in the constant velocity stage movement for detecting the reference pattern, the stage coordinates are inputted in real time (step S23), and simultaneously, the variation in working distance of the electron beam 6 is obtained by the optical ranging mechanism of the focal length measuring part 44. However, in the reference pattern detection processing, the variation in working distance is fed back to the exciting current of the objective lens 24 (step S24). The feedback to the objective lens 24 may be carried out at intervals of time to continuously input 10 frames, i.e., at intervals of 80 msec in this preferred embodiment.

After the stage 3 approaches the coordinates of the reference pattern (step S25), the measuring magnification is set to be a low magnification, e.g., ×15 k (step S26). Then, the input of the SEM image is started at intervals of 8 msec, and the reference pattern recognizing processing is carried out by the pattern dimension calculating part 16 (step S27). At this time, since the stage 3 moves by 80 µm until the elapse of input time (8 msec) of one frame image, the electron beam 6 is scanned by the MOL mechanism as if the stage 3 is stopped relative to the electron beam 6. As described above, since the MOL mechanism is designed to have a movable range of ±350 µm, the MOL mechanism continuously operates over 8 frames. After the reference pattern is recognized, the constant velocity stage movement is continued while being corrected with the alignment pattern (step S28).

3) Measure Pattern Image Inputting Processing

After the reference pattern detection, as shown in FIG. 9, information for the position of the pattern to be measured is derived from the recipe file (step S31), and while the stage 3 is moved toward the position of the pattern to be measured at a constant velocity (step S32), the coordinate position of the stage 3 is inputted from the laser interferometer 41 in real time (step S33).

When it is detected by the laser interferometer 41 that the stage 3 reaches the vicinity of the coordinates of the pattern to be measured (step S34), the measuring magnification is raised at the vicinity of the corresponding position to a high magnification, e.g., ×100 k in this preferred embodiment (step S35).

With respect to the pattern dimension measuring system 10 shown in FIG. 4, the magnification ×15 k is coincident with the width of the frame, 9.6 μm. Therefore, after the reference pattern is recognized, in the phase that the measuring magnification is raised to the high magnification (e.g., ×100 k), a bias voltage is applied in the scanning direction using the MOL mechanism so that the pattern to be measured is arranged at the center of the beam scanning width (1.4 μm by ×100 k). For example, assuming that the outgoing beam axis 7 is Z-axis, the scanning direction is X-axis, and the stage moving direction is Y-axis, then, a voltage corresponding to +320 μm in Y-axis directions is applied to the MOL mechanism of the objective lens 24, so that a voltage corresponding to −320 μm in Y-axis directions is applied to reset the MOL mechanism. In addition, the working distance is corrected on the basis of the measured results of the focal length measuring part 44 (step S36).

Figure 11:
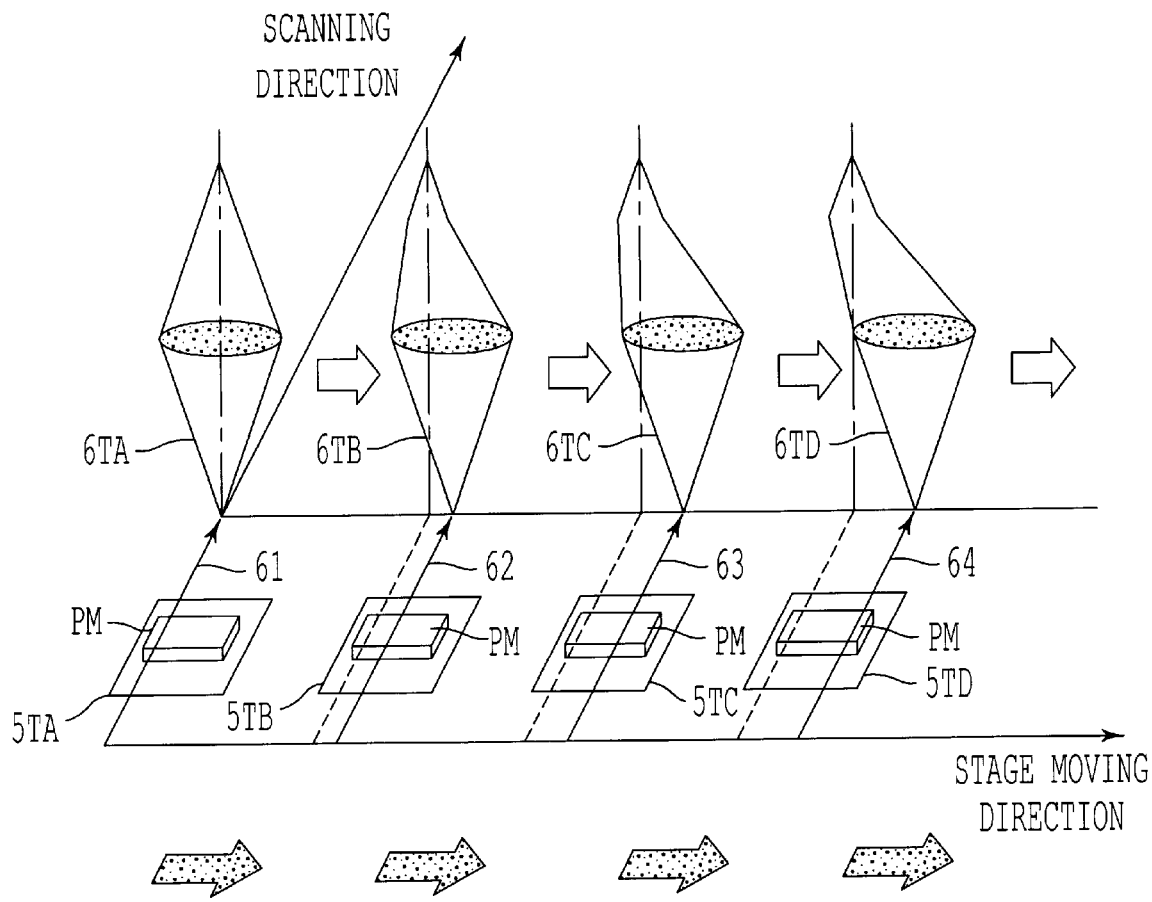
FIG. 11 is a schematic diagram showing an electron beam scanning method in the pattern dimension measuring method shown in FIG. 6.

Since the relationship between the positions of the reference pattern and the pattern to be measured has been calculated from the recipe file by the reference pattern detection processing at step S2, it is possible to calculate the time when the measuring pattern region reaches the region capable of irradiating with the electron beam 6 by the movement of the stage 3. At the same time that it reaches the pattern to be measured, the MOL mechanism is operated in synchronism with the moving speed of the constant velocity stage, so that the electron beam 6 is scanned on the pattern to be measured to continuously input the SEM image (step S37). The relationship between the positions of the stage 3 and the electron beam 6 at this time is schematically shown in FIG. 11. FIG. 11 shows wafers 5ta, 5tb, 5tc and 5td which continue to move at a constant velocity in a direction shown by black arrows (to the right in the figure). These show the respective positions of the same wafer 5 on the same figure at time ta, tb, tc and td, respectively. Electron beams 6ta, 6tb, 6tc and 6td shown in this figure are also emitted from the same electron gun part 11, and show the irradiation positions on the same figure at time ta, tb, tc and td, respectively.

Figure 12:
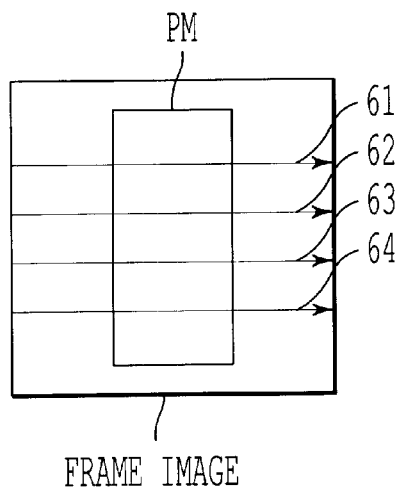
FIG. 12 is a schematic diagram showing an example of a SEM image of a frame acquired by the scanning method shown in FIG. 11.

In the example shown in FIG. 11, the electron beams 6 are scanned in a direction (scanning direction) perpendicular to the stage moving direction by the MOL mechanism while following the movement of the wafer 5 to move a direction shown by blank arrows, so that the electron beam 6 is scanned so as to draw lines 61 through 64 to divide a pattern Pm on the wafer 5 into five parts. That is, the electron beams 6 are scanned so that lines 61, 62, 63 and 64 are loci of the electron beams 6 at times ta, tb, tc and td, respectively. FIG. 12 is a schematic diagram showing an example of a SEM image of a frame (a frame image) acquired by the scanning method shown in FIG. 11. As shown in FIG. 12, the SEM image of the pattern Pm to be measured on the wafer 5 is acquired by four scanning lines having loci of lines 61 through 64.

Since the electron beam 6 is scanned at a speed four times as high as the TV scan, one frame image corresponds to aregion of 1.4 μm. While the MOL mechanism is operated, eight frame images are continuously acquired. Since the relationship between the positions of the reference pattern and a pattern to be measured has been calculated, the pattern to be measured exists in the eight frames.

4) Pattern Dimension Calculating Processing

As shown in FIG. 10, on the basis of the SEM images thus inputted, the pattern dimension calculating part 16 detects a place, at which the pattern to be measured is to be measured, by the pattern recognition (step S41). Thereafter, a line profile at a position corresponding to the place to be measured is derived from the memory 14, the bottom edges of the pattern to be measured are detected by a predetermined measuring algorithm (step S42), and the dimensions of the pattern is calculated (step S43). Furthermore, the setting of the distance between the reference pattern. and the pattern to be measured depends on the time to carry out the pattern recognition processing for the reference pattern. This distance is preferably set so that the reference pattern is spaced from the pattern to be measured by about 500 μm in Y directions, since it usually takes about 50 msec to carry out the pattern recognition processing in the SEM image.

After the input of the image of the pattern to be measured is completed, the MOL mechanism is reset by the above described method. Then, by the laser interferometer 41, the stage coordinates are detected, and the results thereof are inputted to the host computer 4 in real time. In addition, the blanking of the electron beam 6 is carried out until the vicinity of the position of the next pattern to be measured reaches a region where the electron beam 6 is to be scanned, and the constant velocity stage movement is continued while being corrected with the alignment parameters (step S44). Furthermore, the measuring pattern dimension calculating processing must be carried out after the input of the SEM image of the pattern to be measured before the input of the SEM image of the next reference pattern. If this processing time is not in time for the input of the image of the next reference pattern, the dimension calculating rocessing may be carried out after the input of the SEM images of all of the patterns to be measured is completed, or a host computer having an architecture with a multi CPU mounted thereon may be selected.

Figure 13:
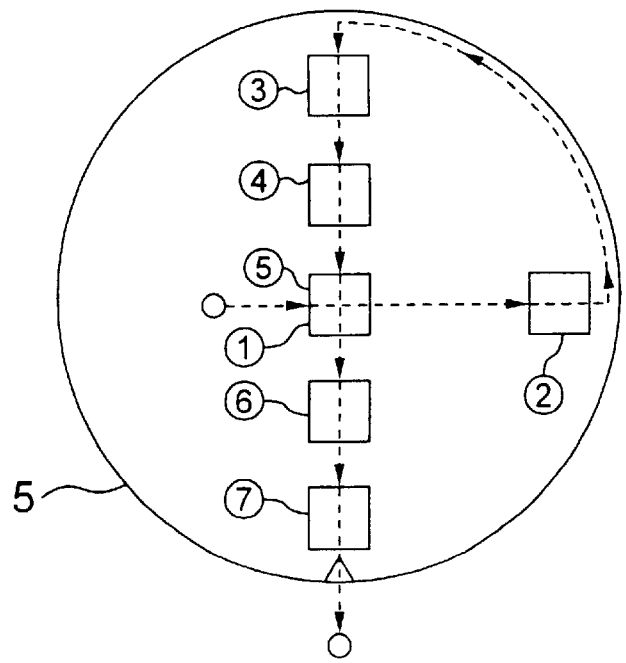
FIG. 13 is a schematic diagram showing the moving locus of a stage of the pattern dimension measuring system shown in FIG. 4.
Figure 14A:
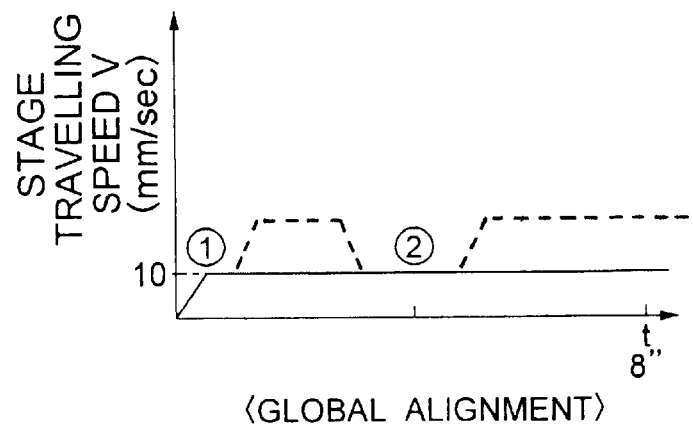
FIGS. 14A and 14B are graphs showing a stage traveling speed when the pattern dimension measuring system shown in FIG. 4 is operated by the pattern dimension measuring method shown in FIG. 6.
Figure 14B:
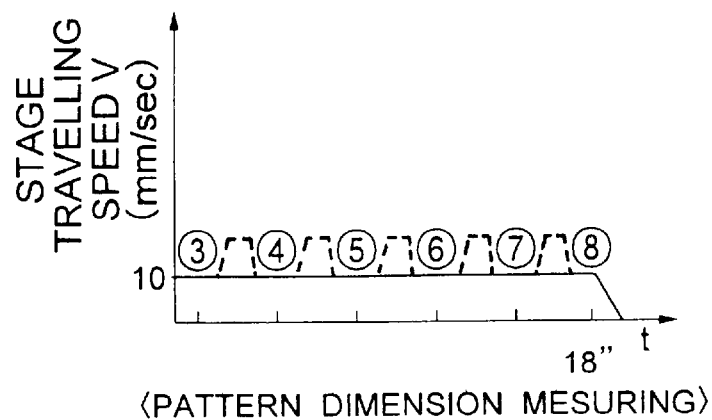

FIGS. 14A and 14B are graphs showing a stage traveling speed when the pattern dimension measuring system 10 is operated by the measuring method in this preferred embodiment. As can be clearly seen from the comparison with FIG. 3A and 3B, it is not required to stop the stage 3 in order to carry out the focusing and pattern recognition. Therefore, it can be understood that the stage 3 can be moved at a constant velocity in any stages from the global alignment processing (FIG. 14A) to the pattern dimension calculating processing (FIG. 14B). Furthermore, although FIG. 13 is the same as FIG. 2, this figure is shown again in order to facilitate better understanding of the operation of the stage 3.

(3) Second Preferred Embodiment of Pattern Dimension Measuring Method

Referring to the flow charts of FIGS. 15 through 18, the second preferred embodiment of a pattern dimension measuring method according to the present invention will be described below. This preferred embodiment is characterized in that an optional pattern on a sample, not the same pattern to be measured, is measured.

Figure 15:
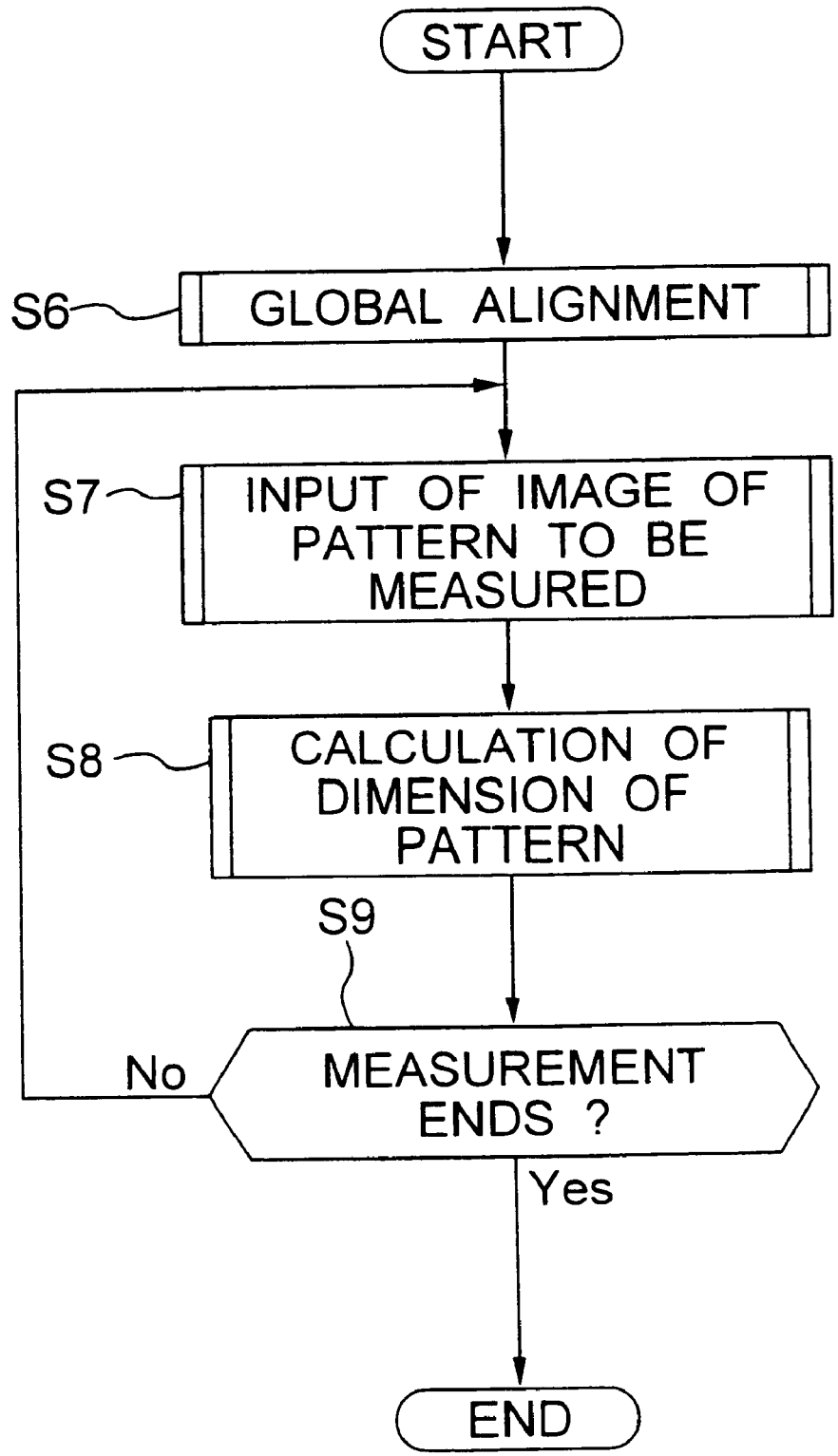
FIG. 15 is a flow chart for schematically explaining the second preferred embodiment of a pattern dimension measuring method according to the present invention.
Figure 16:
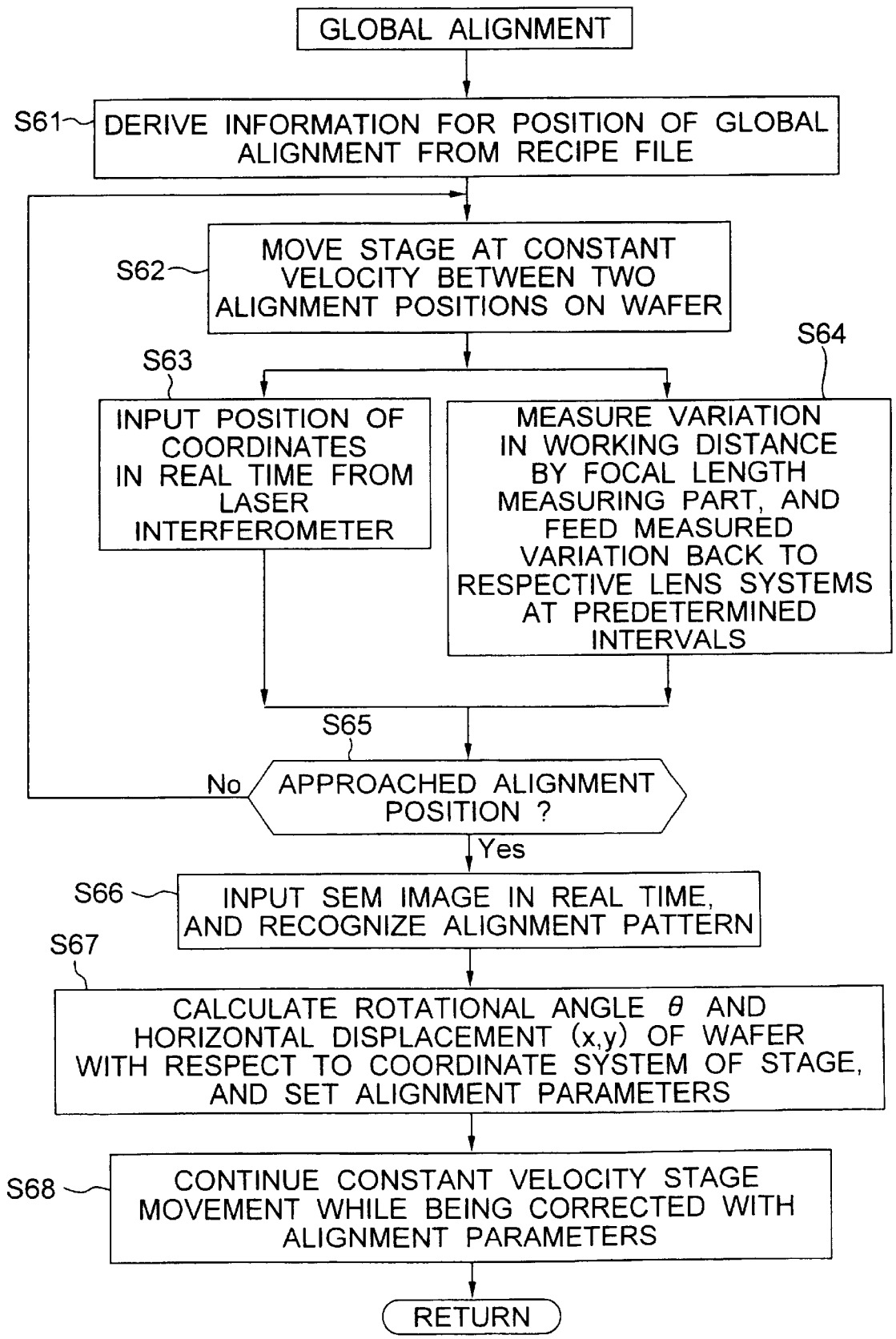
FIG. 16 is a flow chart for explaining the detailed procedure of a global alignment processing in the pattern dimension measuring method shown in FIG. 15.
Figure 17:
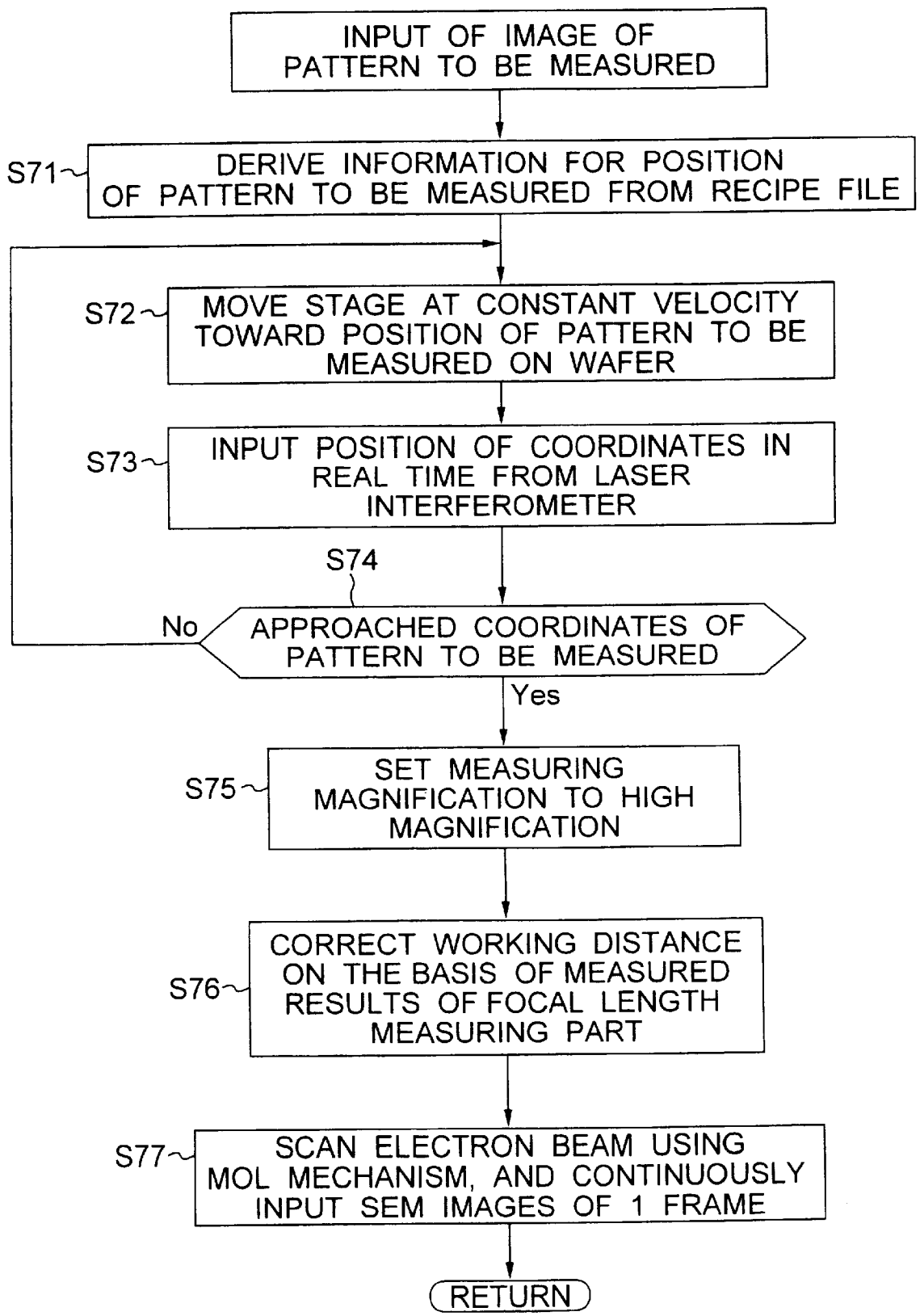
FIG. 17 is a flow chart for explaining the detailed procedure of a measuring pattern image inputting processing in the pattern dimension measuring method shown in FIG. 15.
Figure 18:
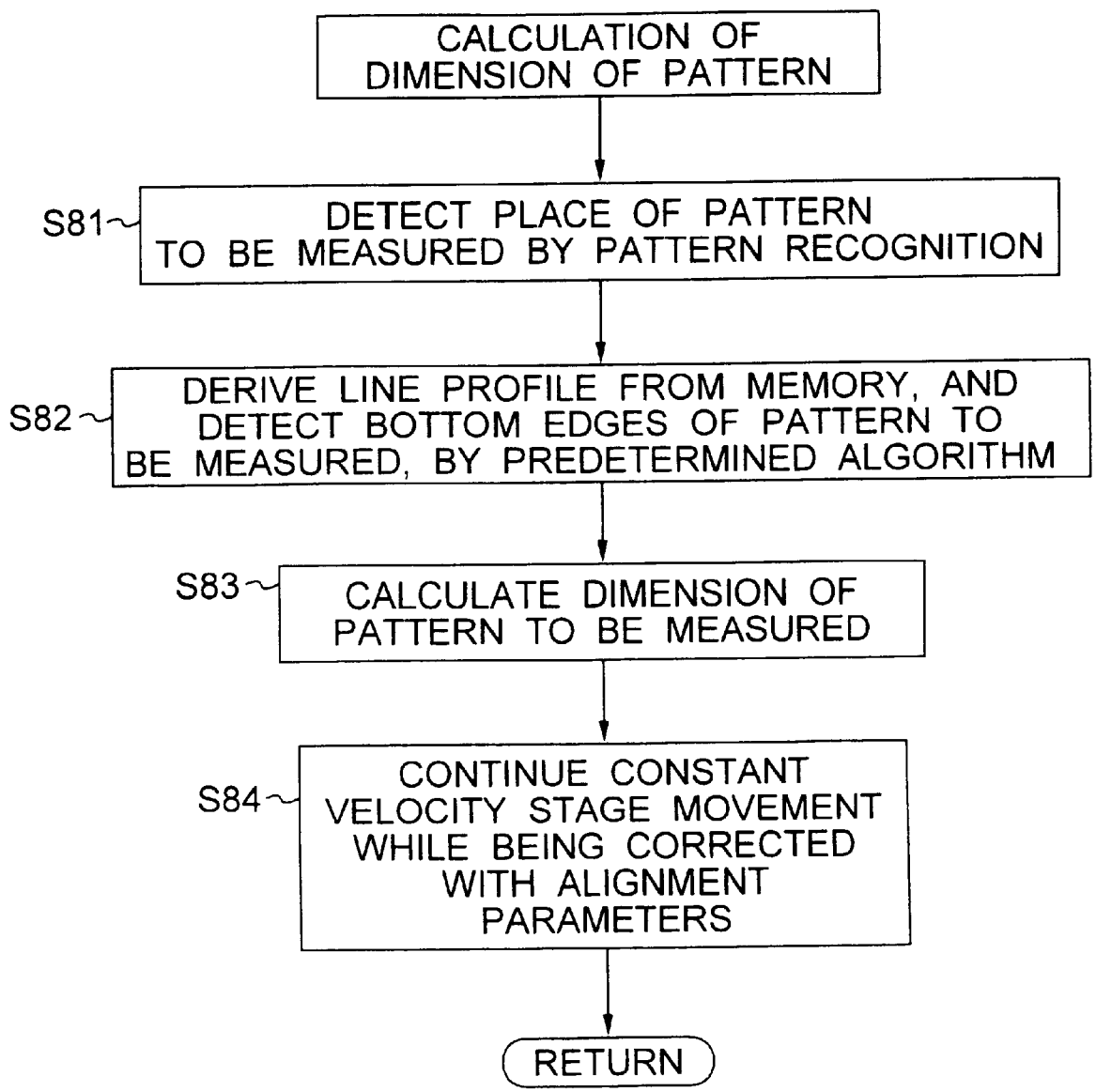
FIG. 18 is a flow chart for explaining the detailed procedure of a pattern dimension calculating processing in the pattern dimension measuring method shown in FIG. 15.

FIG. 15 is a flow chart for explaining the schematic procedure of a pattern dimension measuring method in this preferred embodiment, FIG. 16 is a flow chart for explaining the detailed procedure of a global alignment processing, FIG. 17 is a flow chart for explaining the detailed procedure of a measuring pattern image inputting processing, and FIG. 18 is a flow chart for explaining the detailed procedure of a pattern dimension calculating processing.

As shown in FIG. 15, in this preferred embodiment, a correlation between a pattern layout coordinate system on the wafer 5 and a stage coordinate system is first acquired by a global alignment processing (step S6). Then, the electron beam 6 is scanned in a region, in which the pattern to be measured is formed to carry out a measuring pattern image inputting processing (step S7). On the basis of the image, a pattern dimension calculating processing is carried out (step S8). The above described procedure at steps S7 and S8 is repeated times corresponding to the number of patterns to be measured (step S9).

Referring to the flow charts of FIGS. 16 through 18, the above described procedure at steps S6 through S9 will be described in detail below.

1) Global Alignment Processing

As can be clearly seen from the comparison with FIG. 7, the respective steps of the global alignment in this preferred embodiment shown in FIG. 16 are shown by simply adding 50 to the respective reference numbers of the steps shown in FIG. 7, and substantially the same as those in the above described first preferred embodiment, so that the descriptions thereof are omitted.

2) Measure Pattern Image Inputting Processing

After the global alignment, as shown in FIG. 17, information for the position of the pattern to be measured is derived from the recipe file (step S71), and while the stage 3 is moved toward the position of the pattern to be measured at a constant velocity (step S72), the coordinate position of the stage 3 is inputted from the laser interferometer 41 in real time (step S73).

When it is detected by the laser interferometer 41 that the stage 3 reaches the vicinity of the coordinates of the pattern to be measured (step S74), the measuring magnification is raised at the vicinity of the corresponding position to a high magnification, e.g., ×100 k in this preferred embodiment (step S75).

With respect to the pattern dimension measuring system 10 shown in FIG. 4, the magnification ×15 k is coincident with the width of the frame, 9.6 $\mu$m. Therefore, after the reference pattern is recognized, in the phase that the measuring magnification is raised to the high magnification (e.g., ×100 k), a bias voltage is applied in the scanning direction using the MOL mechanism so that the pattern to be measured is arranged at the center of the beam scanning width (1.4 $\mu$m by ×100 k). For example, assuming that the outgoing beam axis 7 is Z-axis, the scanning direction is X-axis, and the stage moving direction is Y-axis, then, a voltage corresponding to +320 $\mu$m in Y-axis directions is applied to the MOL mechanism of the objective lens 24, so that a voltage corresponding to −320 $\mu$m in Y-axis directions is applied to reset the MOL mechanism. In addition, the working distance is corrected on the basis of the measured results of the focal length measuring part 44 (step S76).

Then, while it reaches the pattern to be measured, the electron beam 6 is scanned on the pattern to be measured by operating the MOL mechanism in synchronism with the constant velocity stage movement, and a SEM image of one frame is inputted (step S77). In this preferred embodiment, since the pattern to be measured is an optional pattern in a cell, the pattern to be measured exists in the frame. Furthermore, in the above description, the SEM image of one frame is inputted. However, when addition of frame images is carried out in order to improve S/N ratio, the MOL mechanism may be operated in the range of ±320 mm to add eight frame images to output a mean value thereof as a pattern dimension.

3) Pattern Dimension Calculating Processing

As shown in FIG. 18, on the basis of the SEM images thus inputted, the pattern dimension calculating part 16 detects a place, at which the pattern to be measured is to be measured, by the pattern recognition (step S81). Thereafter, a line profile at a position corresponding to the place to be measured is derived from the memory 14, the bottom edges of the pattern to be measured are detected by a predetermined measuring algorithm (step S82), and the dimensions of the pattern is calculated (step S83). After the input of the image of the pattern to be measured is completed, the MOL mechanism is reset by the above described method. Then, by the laser interferometer 41, the stage coordinates are detected, and the results thereof are inputted to the host computer 4 in real time. In addition, the blanking of the electron beam 6 is carried out until the vicinity of the position of the next pattern to be measured reaches a region where the electron beam 6 is to be scanned, and the constant velocity stage movement is continued while being corrected with the alignment parameters (step S84).

Referring to FIG. 15 again, when another pattern to be measured exists (step S9), the stage coordinates are detected by the laser interferometer 41, and the results thereof are inputted to the host computer 4 in real time. In addition, the blanking of the electron beam 6 is carried out until the vicinity of the position of the next pattern to be measured reaches a region where the electron beam 6 is to be scanned, and the constant velocity stage movement is continued while being corrected by the alignment parameters. Furthermore, the measuring pattern dimension calculating processing must be carried out after the input of the SEM image of the pattern to be measured before the input of the SEM image of the next reference pattern. If this processing time is not in time for the input of the image of the next reference pattern, the dimension calculating processing may be carried out after the input of the SEM images of all of the patterns to be measured is completed, or a host computer having an architecture with a multi CPU mounted thereon may be selected.

Figure 20:
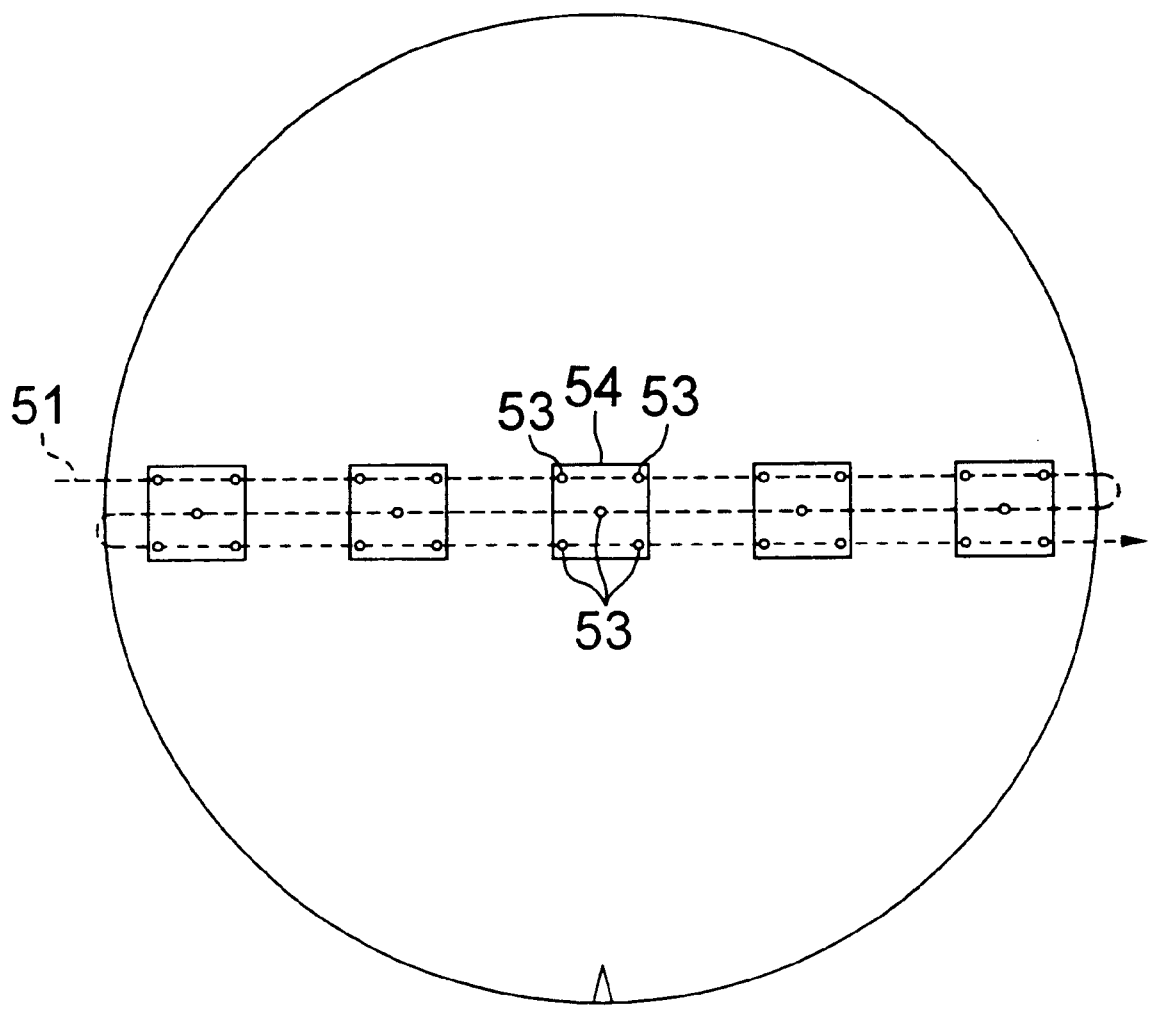
FIG. 20 is a schematic diagram showing an example of a moving locus of a stage in an in-plane 25-point length measurement shown in FIG. 19.

FIG. 19 is a table showing the throughput in the pattern dimension measuring method in this preferred embodiment, in comparison with the prior art. In FIG. 19, pnt denotes a measuring point, and W/Hr denotes the number of wafers to be processed per 1 hour. For example, the expression "in-plane 25-point length measurement (5 pnts/5 shots)" means setting five measuring points 53 for each of measuring shots 54 to measure the dimensions of a pattern, as shown in the schematic diagram of FIG. 20. Furthermore, the dotted line 51 in FIG. 20 shows the moving locus of the stage 3.

It can be seen from FIG. 19 that throughput is improved according to the present invention as the number of measuring points increases.

The throughput of the pattern measuring system in the above described preferred embodiment is determined by the velocity of the constant velocity movement of the stage and the whole travel distance of the stage. Therefore, if the constant velocity is set to be, e.g., double (20 msec), the throughput is also double. Moreover, with respect to the velocity of the constant velocity movement it is also possible to improve throughput by setting the velocity during the input of the images of the reference pattern and pattern to be measured different from the velocity when the input of the images of the next reference pattern and pattern to be measured is started after the input of the image of the pattern to be measured is completed.

While some preferred embodiments of the present invention have been described, the present invention should not be limited to the above described preferred embodiments, but the invention can be embodied in various ways without departing from the scope of the invention.

What is claimed is:

1. A pattern dimension measuring system comprising:
   a movable stage for mounting a sample on the upper surface thereof, said sample having a pattern to be measured formed thereon;

a first control unit for moving said stage;

an electron beam irradiation unit for irradiating said sample with an electron beam;

an electron beam deflecting/scanning unit for deflecting and scanning said electron beam on said sample so that the center of the scanning trajectory on said sample is apart from the beam axis of said electron beam;

a stage coordinate detecting unit for detecting X-Y coordinates of said stage;

a secondary electron detecting unit for detecting a secondary electron and a deflected electron which are emitted from said sample by an irradiation with said electron beam and for outputting an image signal which forms an electron image, said electron image representing a shape of the surface of said sample;

a pattern dimension calculating unit for obtaining a dimension of said pattern to be measured by recognizing side edges thereof using said image signal and by calculating said dimension thereof, and a second control unit for controlling said first control unit so that said stage continuously moves during measurement and for controlling said electron beam deflecting/scanning unit using the detected result of said stage coordinate detecting unit so that the position where the scanning of said electron beam starts moves in synchronism with movement of said stage.

2. A pattern dimension measuring system as set forth in claim 1, wherein said pattern dimension measuring system further comprises a focal length measuring unit for detecting a focal length of said electron beam deflecting/scanning unit, and, said second control unit receives the detected result of said focal length measuring unit and optimizes said focal length of said electron beam deflecting/scanning unit on the basis thereof while said stage moves continuously at a constant velocity.

3. A pattern dimension measuring system as set forth in claim 1, wherein said electron beam deflecting/scanning unit scans each frame to which said pattern to be measured is divided, said frame being defined by the maximum deflection width thereof, and, wherein any one of a continuous scanning mode, in which said plurality of frames are continuously scanned, and a frame accumulating mode, in which the same frame is scanned a plurality of time to output the optimum pattern dimensions, is able to be selected.

4. A pattern dimension measuring system as set forth in claim 1, wherein said second control unit supplies a control signal to said first control unit so that said movable stage moves at a first velocity during acquisition of said image signal and moves at a second velocity which is higher than said first velocity during no acquisition of said image signal.

5. A pattern dimension measuring system as set forth in claim 4, wherein said second control unit sets said second velocity on the basis of a correlation between a distance between said patterns to be measured and on the basis of a processing time required for recognizing a pattern by said pattern dimension calculating unit.

6. A pattern dimension measuring system as set forth in claim 1, which further comprises an image processing unit for processing said image signal so that said electron image is a mirror image with respect to the central axis in X or Y directions in accordance with a variation in moving direction of said stage.

7. A pattern dimension measuring method using a pattern dimension measuring system comprising:

a movable stage for mounting thereon a sample, on which a pattern to be measured is formed;

a stage coordinate detecting unit for detecting X-Y coordinates of said stage;

a electron beam irradiation unit for irradiating said sample with an electron beam;

an electron beam deflecting/scanning unit for deflecting and scanning said electron beam on said sample;

a focal length measuring unit for detecting a focal length of said electron beam deflecting/scanning unit;

a secondary electron detecting unit for detecting a secondary electron and a deflected electron which are emitted from said sample by the irradiation with said electron beam and for outputting an image signal which forms an electron image; and a pattern dimension calculating unit for calculating a dimension of said pattern by recognizing side edges of said pattern using said image signal and by calculating said dimension of said pattern, said pattern dimension measuring method comprising:

calculating a correlation between a coordinate system of said stage and a pattern layout coordinate system;

detecting the position of a pattern to be measured on the basis of said correlation while said stage moves continuously during measurement;

detecting the variation in distance between said sample and said electron beam irradiation unit due to the variation on the surface of said sample using the focal length detected by said focal length measurement unit and optimizing the focal length of said electron beam deflecting/scanning unit before said pattern to be measured reaches a location at which said electron beam is scanned in consequence of movement of said movable stage;

acquiring an electron image of said pattern to be measured by deflecting and scanning said electron beam in synchronism with the movement of said movable stage so that the center of the scanning trajectory on said sample is apart from the beam axis of said electron beam; and recognizing said pattern to be measured using said electron image and calculating the dimensions thereof by a predetermined algorithm.

8. A pattern dimension measuring method as set forth in claim 7, wherein said pattern includes a reference pattern serving as a reference of the detection of the pattern to be measured, said correlation includes a relationship between a position of said reference pattern and a position of said pattern to be measured, said detecting of the position of said pattern to be measured includes detecting the position of said reference pattern on the basis of said correlation, and the position of said pattern is measured on the basis of the detected position of said reference pattern and said relationship between the detected position of said reference pattern and the position of said pattern to be measured.

9. A pattern dimension measuring method as set forth in claim 7, wherein acquiring of the electron image of said pattern to be measured includes dividing the region of said pattern to be measured to a plurality of frames and continuously scanning said plurality of frames, said frame being defined by the maximum deflection width of said electron beam deflecting/scanning unit.

10. A pattern dimension measuring method as set forth in claim 7, wherein acquiring of the electron image of said pattern to be measured includes dividing the region of said pattern to be measured to a plurality of frames and scanning the same frame a plurality of times and outputting an optimum pattern dimension, said frame being defined by the maximum deflection width of said electron beam deflecting/scanning unit.

11. A pattern dimension measuring method as set forth in claim 7, wherein said stage is moved at a first velocity during acquisition of said image signal and is moved at a second velocity which is higher than said first velocity during no acquisition of said image signal.

12. A pattern dimension measuring method as set forth in claim 11, wherein said second velocity is set on the basis of a correlation between a distance between said patterns to be measured and on the basis of a processing time required for recognizing a pattern by said pattern dimension calculating unit.

13. A pattern dimension measuring method as set forth in claim 7, wherein said fourth step includes a step of processing said image signal so that said electron image is a mirror image with respect to the central axis in X or Y directions in accordance with a variation in moving direction of said stage.

14. A pattern dimension measuring method as set forth in claim 7, wherein said second step is a step of detecting a position of said pattern to be measured, at a first measuring magnification, and, said fourth step is a step of acquiring said electron image at a second measuring magnification which is greater than said first measuring magnification.

* * * * *